(12) United States Patent
Lubowski et al.

(10) Patent No.: US 11,524,140 B2
(45) Date of Patent: Dec. 13, 2022

(54) METHOD AND APPARATUS FOR RECTAL ANAESTHESIA

(71) Applicant: New Medtek Devices Pty Ltd, Sydney (AU)

(72) Inventors: David Zachary Lubowski, Edgecliff (AU); Robert Tiller, Birchgrove (AU)

(73) Assignee: New Medtek Devices Pty Ltd, Sydney (AU)

( * ) Notice: Subject to any disclaimer, the term of this patent is extended or adjusted under 35 U.S.C. 154(b) by 0 days.

(21) Appl. No.: 16/971,115

(22) PCT Filed: Feb. 27, 2019

(86) PCT No.: PCT/AU2019/050165
§ 371 (c)(1),
(2) Date: Aug. 19, 2020

(87) PCT Pub. No.: WO2019/165500
PCT Pub. Date: Sep. 6, 2019

(65) Prior Publication Data
US 2021/0085922 A1     Mar. 25, 2021

(30) Foreign Application Priority Data
Feb. 28, 2018 (AU) ................................ 2018900653

(51) Int. Cl.
*A61M 25/00* (2006.01)
*A61N 1/05* (2006.01)
(Continued)

(52) U.S. Cl.
CPC ....... *A61M 25/0097* (2013.01); *A61B 5/4893* (2013.01); *A61M 25/0026* (2013.01);
(Continued)

(58) Field of Classification Search
CPC .................. A61B 9/005; A61B 5/1106; A61B 2017/3452; A61M 25/0194;
(Continued)

(56) References Cited

U.S. PATENT DOCUMENTS

2002/0133121 A1     9/2002  Bierman
2003/0208166 A1*   11/2003  Schwartz .............. A61M 25/00
                                                                   604/266
(Continued)

FOREIGN PATENT DOCUMENTS

WO     2016178804 A1     11/2016

OTHER PUBLICATIONS

International Search Report and Written Opinion issued in International Application No. PCT/AU2019/050165 dated May 13, 2019 (16 pages).

*Primary Examiner* — Bhisma Mehta
*Assistant Examiner* — Phoebe Anne Staton
(74) *Attorney, Agent, or Firm* — Bookoff McAndrews, PLLC

(57) ABSTRACT

A system and method for delivering a medicament including a catheter configured for implantation in different target tissue sites, extending from a proximal end to a distal end, and having a sidewall which defines an internal lumen. The distal end has one or more apertures in the sidewall for the release of the medicament into the target tissue site; the system also comprises a medicament reservoir fluidly communicable with the internal lumen of each catheter, an adhesive member configured to adhere to the skin of the patient around the exit wound and having an opening therein to allow the catheters to pass through the adhesive member and a retaining member configured to be overlaid on the adhesive member and comprising a guide surface configured to receive a length of the two or more catheters and a
(Continued)

plurality of retaining portions to retain the catheters against the guide surface.

16 Claims, 20 Drawing Sheets

(51) Int. Cl.
    *A61N 1/36*     (2006.01)
    *A61M 25/01*     (2006.01)
    *A61M 25/02*     (2006.01)
    *A61B 5/00*     (2006.01)
    *A61M 39/02*     (2006.01)

(52) U.S. Cl.
    CPC .... *A61M 25/0155* (2013.01); *A61M 25/0194* (2013.01); *A61M 25/02* (2013.01); *A61N 1/0512* (2013.01); *A61N 1/36007* (2013.01); *A61M 2025/0031* (2013.01); *A61M 2025/0166* (2013.01); *A61M 2025/0177* (2013.01); *A61M 2025/024* (2013.01); *A61M 2025/0213* (2013.01); *A61M 2025/0253* (2013.01); *A61M 2039/0267* (2013.01); *A61M 2202/048* (2013.01); *A61M 2205/04* (2013.01); *A61M 2205/3334* (2013.01); *A61M 2210/1067* (2013.01)

(58) Field of Classification Search
    CPC ...... A61M 2205/04; A61M 2205/3334; A61M 2210/1067; A61M 25/01; A61M 19/00; A61M 2025/0206
    See application file for complete search history.

(56) References Cited

U.S. PATENT DOCUMENTS

| | | |
|---|---|---|
| 2005/0033372 A1 | 2/2005 | Gerber |
| 2007/0173900 A1* | 7/2007 | Siegel ................ A61B 17/3468 607/41 |
| 2008/0243082 A1 | 10/2008 | Goodman |
| 2009/0043260 A1 | 2/2009 | Bierman |
| 2015/0088075 A1 | 3/2015 | Khalaj |
| 2016/0136395 A1 | 5/2016 | Hsu et al. |
| 2017/0056630 A1 | 3/2017 | Fee |

* cited by examiner

METHOD AND APPARATUS FOR RECTAL ANAESTHESIA

CROSS-REFERENCE TO RELATED APPLICATIONS

This application is the U.S. national phase entry under 35 U.S.C. § 371 of International Application No. PCT/AU2019/050165, filed on Feb. 27, 2019, which claims priority to Australian Patent Application No. 2018900653, filed on Feb. 28, 2018.

FIELD OF THE INVENTION

The present invention relates to a method and apparatus for the management of patient pain after a hemorrhoidectomy or similar surgery through nerve anaesthesia. More specifically, the invention relates to an implantable catheter device for the delivery of an anaesthetic to an area of tissue around a nerve of a patient following a hemorrhoidectomy or similar surgery.

BACKGROUND

Haemorrhoids are enlarged prolapsing anal cushions which can result in bleeding, itching, and pain and which affect more than 50% of people at some point in their lives.

The treatment for haemorrhoids includes application of topical ointments and/or suppositories, injection with sclerosants, rubber band ligation, stapled haemorrhoidopexy and in severe cases may involve surgery to physically remove the haemorrhoids. The surgical removal of haemorrhoids is known as a hemorrhoidectomy and the procedure involves the patient receiving either local or general anaesthesia. Incisions are made in the tissue around the haemorrhoid. The vessels inside the haemorrhoid are tied off to prevent bleeding, and the haemorrhoid is removed.

Hemorrhoidectomy is considered an "outpatient procedure", wherein the patient is typically released from hospital to return home within 24 hours of the procedure. Because of the extensive network of nerves within the anal canal, postoperative pain can be significant for the patient.

Currently, after hemorrhoidectomy surgery, local anaesthetic is injected into the area immediately after surgery and lasts for up to 24 hours. The patient is then given oral opioids/narcotics to manage pain which ensues for many weeks. Complete recovery from the procedure can vary between patients, taking between 2 weeks to 2 months.

Severe postoperative pain not only requires opioid use, which may have unwanted risks and side effects, but may also prolong the hospital stay, and affect the comfort and wellbeing of the patient.

It is therefore desirable to provide a method and apparatus for the controlled delivery of a medicament such as an anaesthetic to a nerve branch of a patient following a hemorrhoidectomy, or similar (other) surgery of the anal canal.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

In one aspect, the disclosure provides a system for delivering a medicament to a target tissue site in a patient over a period of time, the system comprising:

a catheter configured for implantation in a target tissue site, the catheter extending from a proximal end to a distal end and having a sidewall which defines an internal lumen, said distal end having one or more apertures in the sidewall for the release of the medicament into the target tissue site;

a medicament reservoir fluidly communicable with the internal lumen of the catheter;

an adhesive member configured to adhere to the skin of the patient around the exit wound and having an opening therein to allow the catheter to pass through the adhesive member; and a retaining member configured to be overlaid on the adhesive member and comprising a guide surface configured to receive a length of the catheter and a plurality of retaining portions to retain the catheters against the guide surface.

In another aspect, the disclosure provides a system for delivering a medicament to a target tissue site in a patient over a period of time, the system comprising:

two or more catheters configured for implantation in different target tissue sites, each catheter extending from a proximal end to a distal end and having a sidewall which defines an internal lumen, said distal end having one or more apertures in the sidewall for the release of the medicament into the target tissue site;

a reservoir of the medicament fluidly communicable with the internal lumen of each catheter;

an adhesive member configured to adhere to the skin of the patient around the exit wound and having an opening therein to allow the catheters to pass through the adhesive member; and a retaining member configured to be overlaid on the adhesive member and comprising a substantially flat base, a guide surface configured to receive a length of the two or more catheters and a plurality of retaining portions to retain the catheters against the guide surface.

A further aspect of the disclosure provides a method for treating pain in a patient after haemorrhoid surgery, the method including:

providing two or more catheters, each catheter extending from a proximal end to a distal end and having a sidewall which defines an internal lumen, said distal end having one or more apertures in the sidewall for the release of the medicament into a target tissue site;

advancing the two or more catheters from an entry incision on the skin until the distal end of one catheter is positioned in a first target tissue site and the distal end of the second catheter is positioned in a second, different target tissue site;

connecting the proximal ends of the catheters to a medicament reservoir and actuating delivery of the medicament to the first and the second target tissue sites.

A further aspect of the disclosure provides a method for implanting a catheter to deliver medicament to a patient after haemorrhoid surgery, the method including:

providing a catheter which extends from a proximal end to a distal end and has a sidewall which defines an internal lumen, said distal end having one or more apertures in the sidewall for the release of the medicament into a target tissue site;

connecting a distal end of the catheter to a stimulator trocar, the stimulator trocar comprising an elongate body which is made from a material having a greater rigidity than the catheter, the stimulator trocar comprising a nerve stimulator configured to stimulate nerves in a target tissue site;

advancing the stimulator trocar and the catheter through the tissue of the patient;

actuating the nerve stimulator at a determined frequency and adjusting the positioning of the stimulator trocar and the distal end of the catheter until a physical contraction of the external anal sphincter is observed at a frequency that correlates with the determined frequency of the nerve stimulator;

identifying the location of the nerve stimulator and the distal end of the catheter where physical contraction of the external anal sphincter is achieved;

disconnecting the nerve stimulator from the catheter and withdrawing the nerve stimulator through the first incision leaving the distal end of the catheter implanted in the target tissue site.

A further aspect of the disclosure provides a method for positioning a catheter in a target tissue site to deliver a medicament to a patient after haemorrhoid surgery, the method including:

providing a catheter which extends from a proximal end to a distal end and has a sidewall which defines an internal lumen, the distal end of the catheter having one or more apertures in the sidewall for the release of the medicament to the target tissue site;

making a lateral incision in the skin of the thigh of the patient and a first incision on one side of the anus;

tunnelling a trocar from the lateral incision through the tissue and towards the first incision;

at the first incision, connecting a tip of the trocar to the proximal end of the catheter and withdrawing the trocar towards the lateral incision until a desired length of the catheter is pulled through, and extends from, the lateral incision and the distal end of the catheter extends from the first incision;

connecting the distal end of the catheter to a stimulator trocar, the stimulator trocar comprising an elongate body which is made from a material having a greater rigidity than the catheter, the stimulator trocar comprising a nerve stimulator configured to stimulate nerves in the target tissue site;

advancing the stimulator trocar and the catheter through the tissue of the patient;

actuating the nerve stimulator at a determined frequency and adjusting the positioning of the stimulator trocar and the distal end of the catheter until a physical contraction of the external anal sphincter is observed at a frequency that correlates with the determined frequency of the nerve stimulator;

identifying the location of the nerve stimulator and the distal end of the catheter where physical contraction of the external anal sphincter is achieved;

disconnecting the nerve stimulator from the catheter and withdrawing the nerve stimulator through the first incision leaving the distal end of the catheter implanted in the first target tissue site;

connecting the proximal end of the catheter to a reservoir of medicament and infusing the medicament through the internal lumen of the catheter to deliver the medicament to the target tissue site.

A second catheter may be inserted into a different target tissue site. The second catheter extends from a proximal end to a distal end and has a sidewall which defines an internal lumen, the distal end of the second catheter having one or more apertures in the sidewall for the release of the medicament to the target tissue site. In this embodiment, a second incision in the skin is made on the opposite side of the anus to the first incision and a trocar is tunnelled through the tissue from the lateral incision and across the midline of the patient towards the second incision;

at the second incision, connecting the tip of the trocar to the proximal end of the second catheter and withdrawing the trocar until a desired length of the second catheter is pulled through, and extends from, the lateral incision and the distal end of the second catheter extends from the second incision;

connecting the distal end of the second catheter to a stimulator trocar;

advancing the stimulator trocar and the second catheter through the tissue of the patient;

actuating the nerve stimulator at a determined frequency and adjusting the positioning of the stimulator trocar and the distal end of the second catheter until a physical contraction of the external anal sphincter is observed at a frequency that correlates with the determined frequency of the nerve stimulator; identifying the location of the nerve stimulator and the distal end of the second catheter where physical contraction of the external anal sphincter is achieved;

disconnecting the nerve stimulator from the second catheter and withdrawing the nerve stimulator through the first incision leaving the distal end of the second catheter implanted in the first target tissue site;

connecting the proximal end of the second catheter to a reservoir of medicament and infusing the medicament through the internal lumen of the second catheter to deliver the medicament to the target tissue site.

In another aspect, there is provided a method for positioning a catheter in a target tissue site to deliver a medicament to a patient after haemorrhoid surgery, the method including:

providing a catheter which extends from a proximal end to a distal end and has a sidewall which defines an internal lumen, the distal end of the catheter having one or more apertures in the sidewall for the release of the medicament to the target tissue site;

making a lateral incision in the skin of the thigh of the patient and a first incision on one side of the anus;

tunnelling a trocar from the first incision through the tissue and towards the lateral incision;

at the lateral incision, connecting a tip of the trocar to the distal end of the catheter and pulling the trocar towards the first incision until a desired length of the catheter is pulled through, and extends from, the first incision and the proximal end of the catheter extends from the lateral incision;

connecting the distal end of the catheter to a stimulator trocar, the stimulator trocar comprising an elongate body which is made from a material having a greater rigidity than the catheter, the stimulator trocar comprising a nerve stimulator configured to stimulate nerves in the target tissue site;

advancing the stimulator trocar and the catheter through the tissue of the patient;

actuating the nerve stimulator at a determined frequency and adjusting the positioning of the stimulator trocar and the distal end of the catheter until a physical contraction of the external anal sphincter is observed at a frequency that correlates with the determined frequency of the nerve stimulator;

identifying the location of the nerve stimulator and the distal end of the catheter where physical contraction of the external anal sphincter is achieved;

disconnecting the nerve stimulator from the catheter and withdrawing the nerve stimulator through the first incision leaving the distal end of the catheter implanted in the target tissue site;

connecting the proximal end of the catheter to a reservoir of medicament and infusing the medicament through the internal lumen of the catheter to deliver the medicament to the target tissue site.

A second catheter may be inserted into a different target tissue site. The second catheter extends from a proximal end to a distal end and has a sidewall which defines an internal lumen, the distal end of the second catheter having one or more apertures in the sidewall for the release of the medicament to the target tissue site. In this embodiment, a second incision in the skin is made on the opposite side of the anus to the first incision and a trocar is tunnelled through the tissue from the second incision and across the midline of the patient towards the lateral incision;

tunnelling a trocar from the second incision through the tissue, across the midline of the patient and towards the lateral incision;

at the lateral incision, connecting a tip of the trocar to the distal end of the second catheter and pulling the trocar towards the second incision until a desired length of the catheter is pulled through, and extends from, the second incision and the proximal end of the second catheter extends from the lateral incision;

connecting the distal end of the catheter to a stimulator trocar, the stimulator trocar comprising an elongate body which is made from a material having a greater rigidity than the second catheter, the stimulator trocar comprising a nerve stimulator configured to stimulate nerves in the target tissue site; advancing the stimulator trocar and the catheter through the tissue of the patient;

actuating the nerve stimulator at a determined frequency and adjusting the positioning of the stimulator trocar and the distal end of the second catheter until a physical contraction of the external anal sphincter is observed at a frequency that correlates with the determined frequency of the nerve stimulator;

identifying the location of the nerve stimulator and the distal end of the second catheter where physical contraction of the external anal sphincter is achieved;

disconnecting the nerve stimulator from the distal end of second catheter and withdrawing the nerve stimulator through the second incision leaving the distal end of the second catheter implanted in the target tissue site;

connecting the proximal end of the second catheter to a reservoir of medicament and infusing the medicament through the internal lumen of the second catheter to deliver the medicament to the target tissue site.

In another aspect, the disclosure provides a surgical kit comprising:

two or more catheters configured for implantation in a target tissue site of a patient, each catheter extending from a proximal end to a distal end and having a sidewall which defines an internal lumen, said distal end having one or more apertures in the sidewall;

an adhesive member configured to adhere to the skin of the patient around the exit wound and having an aperture therein to allow the catheters to pass through the adhesive member;

an open ring-shaped retaining member configured to be overlaid on the adhesive member and comprising a substantially flat base, a guide surface configured to receive a length of the two or more catheters and a plurality of retaining portions to retain the catheters against the guide surface;

a tunnelling trocar configured for attachment to the proximal ends of the catheters;

a stimulator trocar comprising an elongate body which is made from a material having a greater rigidity than the two or more catheters, the stimulator trocar comprising a nerve stimulator configured to stimulate nerves in a target tissue site;

a pump and a medicament reservoir;

a sheet for application to the patient's skin around the surgical site, the sheet having an adhesive surface for adhering to the skin of the patient and a series of frangible regions for removal of parts of the sheet.

A retainer for securing one or more catheters at an exit wound site of a patient, the retainer comprising a retainer body having a lower, skin facing surface and an opposed guide surface configured to receive one or more catheters, the retainer further comprising a plurality of clips to secure a length of the one or more catheters to the retainer.

The guide surface may be curved and terminate in an outer rim. The clips may be formed integrally with the retainer body or may be a separate structure which clip onto the body.

The retainer may engage with a housing. The housing may comprise a circular base having an outer facing surface and a substantially flat inner surface. An outer rim may extend from the circular base and terminate in a peripheral lip. The peripheral lip is configured to attach to the rim of the retainer body to secure the two parts together. A plurality of arms may extend inwardly and upwardly from an inner edge of the circular base. The arms may terminate in a central body. The central body may comprise a substantially solid circular structure.

In another aspect, there is provided a trocar comprising an elongate, substantially solid body extending from a proximal end to a distal end, the distal end of the trocar having a tissue separating tip and a hook feature to capture part of another medical instrument.

In a further aspect, the disclosure provides an implantable catheter for the delivery of a medicament to a target tissue site, the catheter extending from a proximal end to an open distal end and having a sidewall which defines an internal lumen, said catheter having one or more apertures in the sidewall adjacent to the distal end, the apertures forming a fluid flow path from the internal lumen to an exterior of the catheter, the catheter further comprising a trocar receiving opening positioned proximal to the open distal end and sized to receive part of a trocar.

In a further aspect, the disclosure provides an implantable catheter for the delivery of a medicament to a target tissue site, the catheter extending from a proximal end to an open distal end and having a sidewall which defines an internal lumen, said catheter having one or more apertures in the sidewall adjacent to the distal end, the apertures forming a fluid flow path from the internal lumen to an exterior of the catheter, the catheter further comprising a trocar receiving opening positioned at the proximal end, the opening sized to receive part of a trocar.

In another aspect, the disclosure provides a nerve stimulating trocar comprising an elongate, substantially solid body having a proximal region, a distal region terminating in a tip and an intermediate region between the proximal and distal regions, the nerve stimulating trocar further including a nerve stimulating electrode connectable to an energy source and extending distally along a length of the nerve stimulating trocar, terminating at a stimulation region beyond, at or proximal to the tip, wherein the proximal region has an inner curved surface to conform with the outer surface of a substantially cylindrical medical instrument, the intermediate region forming a bend in the trocar body such that a main axis of the proximal region is substantially parallel to a main axis of the distal region.

A further aspect discloses a wearable apparatus for delivery of a medicament to a patient, the apparatus comprising:

a belt attachable to the patient;

a channel extending within or along a surface of the belt;

a catheter fluidly connected to the channel and extending from the belt, the catheter having a sidewall which defines an internal lumen and wherein further, the sidewall of the catheter includes one or more openings which define a fluid flow path from the internal lumen to the outside of the catheter;

a pump;

wherein the medicament is held in the channel and the pump is configured to pump the medicament from the channel and into the internal lumen of the catheter.

The target tissue site may comprise tissue adjacent to the anal and/or rectal branches of the pudendal nerves although any site adjacent to nerve of interest is envisaged. The first target tissue site may comprise tissue around the left pudendal nerve and the second target tissue site may comprise tissue around the right pudendal nerve or vice versa.

The medicament to be delivered may be an analgesic. The analgesic may include but is not limited to bupivacaine, lidocaine, ropivacaine, opioid analgesics such as buprenorphine, hydromorphone, ketobemidone, levomethadyl, levorphanol, mepiridine, methadone, morphine, nalbuphine, opium, oxycodone, pentazocine, phenoperi-dine, butorphanol, dextromoramide, dezocine, dextropropoxyphene, diamorphine, fentanyl, alfentanil, sufentanil, hydrocodone, piritramide, dextropropoxyphene, remifentanil, sufentanil, tilidine, tramadol, codeine, dihydrocodeine, meptazinol, dezocine, eptazocine, flupirtine or a combination thereof.

Typically the analgesic is ropivacaine. The ropivacaine may be delivered in solution with a concentration of 0.25%, or 0.5% or 0.75%. The ropivacaine may be in a concentration of between 0.25 to 0.5% or 0.5% to 0.75%. In some embodiments, the concentration of ropivacaine may exceed 0.75%.

The analgesic may be delivered at a dose of 20 mls per day (24 hours). Alternatively, the analgesic may be delivered at a dose of 1 ml or 5 ml or 10 mls or 15 mls or 25 mls or 30 mls per day. The dose may, in some embodiments exceed 30 mls per day including 40 mls, 50 mls, 60 mls, 70 mls, 80 mls, 90 mls or 100 mls per day.

The analgesic may be delivered to the patient continuously over the time period. Alternatively, it may be delivered in dosage intervals within the time period. The dosage intervals may occur every 1, 5, 10, 20, 30, 40 or 50 minutes. Further, the dosage intervals may occur hourly, every 2 hours, every 3 hours, every 4 hours, every 5 hours, every 6 hours, every 7 hours, every 8 hours, every 9 hours, every 10 hours, every 11 hours or every 12 hours.

The dosage intervals may range of from 30 secs up to 6 hours. The dosage intervals may be 30 minutes, 1 hour, 2 hours, 3 hours, 4 hours, 5 hours of 6 hours. In some cases, the dosage intervals may be longer than 6 hours. For example the dosage interval may be 7 hours, 8 hours, 9 hours, 10 hours, 11 hours or 12 hours. Further, the dosage intervals may exceed 12 hours and may be from 12 hours to 23 hours.

The time period may range from 1 day to 3 months. For example, the time period may be 1 week, 2 weeks, 3 weeks, 4 weeks, 5 weeks, 6 weeks, 7 weeks, 2 months or 3 months.

The analgesic may be delivered in an initial burst followed by continuous delivery thereafter or alternatively followed by dosage intervals.

The initial burst may enable a larger initial dose to be delivered over an initial period of time to achieve an immediate pain relief for the patient. The initial burst may deliver a percentage of the daily dose. For example, the initial burst may deliver 10%, 20%, 30%, 40%, 50%, 60%, 70%, 80% or 90% of the daily dose. The regimen may be such that such an initial burst occurs daily, or every second, third, fourth, fifth or sixth day during the time period. Further, an initial burst may occur once every week, every 2 weeks, every three weeks Alternatively, an initial burst may only occur once, for example, on the first day of treatment.

In a preferred embodiment, the catheters are relatively flexible. However, the catheters may have sufficient rigidity so as to permit passage through the body to the target tissue site.

The catheters may be made from one or more biodegradable polymers including but not limited to: polylactic acid, polyglycolic acid, poly(L-lactide), poly(D,L-lactide), polyglycolic acid, poly(L-lactide-co-D,L-lactide), poly(L-lactide-co-glycolide), poly(D, L-lactide-co-glycolide), poly (glycolide-co-trimethylene carbonate), poly(D,L-lactide-co-caprolactone), poly(glycolide-co-caprolactone), polycaprolactone, polycaprolactone co-butylacrylate, polyhydroxybutyrate, poly(phosphazene), poly(phosphate ester), poly(amino acid), polydepsipeptide, maleic anhydride copolymer, polyiminocarbonates, poly[(97.5% dimethyl-trimethylene carbonate)-co-(2.5% trimethylene carbonate)], poly (orthoesters), tyrosine-derived polyarylate; polyethylene oxide, polyoxaester, polydioxanone, polypropylene fumarate, poly(ethyl glutamate-co-glutamic acid), poly(tert-butyloxy-carbonylmethyl glutamate).

In some embodiments, the catheters may be made from one or more non-biodegradable materials including, but not limited to, various cellulose derivatives (carboxymethyl cellulose, cellulose acetate, cellulose acetate propionate, ethyl cellulose, hydroxypropyl methyl cellulose, and alkyl celluloses), silicon and silicon based polymers (such as polydimethylsiloxane), polyethylene-co-(vinyl-acetate), poloxamer, polyvinylpyrrolidone, poloxamer, polyvinylpyrrolidone, poloxamine, polypropylene, polyamide, polyacetal, polyester, poly ethyl-ene-chlorotrifluoroethylene, polytetrafluoroethylene (PTFE or "Teflon™"), styrene butadiene rubber, polyethylene, polypropylene, polyphenylene oxide-polystyrene, poly-chloro-p-xylene, polymethylpentene, polysulfone, non-degradable ethylene-vinyl acetate, and other related bio-stable polymers.

The catheters may have a lubricious outer coating to aid in delivery towards the target tissue site. The catheter coating may also comprise one or more drugs selected from the group consisting of antimicrobial agents, anti-inflammatory agents, anti-scarring agents, anti-fibrotic agents and leukotriene inhibitors.

The overall shape of the catheters may comprise an elongated tube. The catheters may be of the same diameter relative to each other or different diameters relative to each other. In one embodiment the catheters may have a diameter in the range of 2 mm to 10 mm. Specifically, the catheters have a diameter of approximately 2 mm, 3 mm, 4 mm, 5 mm, 6 mm, 7 mm, 8 mm, 9 mm or 10 mm.

The one or more apertures may be positioned at or adjacent to the distal end of the catheters. The catheters may comprise a single aperture at or adjacent the distal end. Alternatively the catheters may include a plurality of apertures at or adjacent the distal end. The plurality of apertures may be positioned around the circumference of the catheters.

The apertures may be evenly spaced relative to each other or unevenly spaced. Further, the apertures may be arranged in ring-like arrangements around the circumference of the catheters. The apertures may extend a length of the catheter from the distal end. Alternatively, the apertures may be positioned along one side of a catheter. In such an embodiment, the catheter may be oriented during use such that the apertures are adjacent and facing the nerve or nerve branch.

The apertures of a catheter may be arranged in a number of configurations in addition to the ring like arrangement described above. For example, the apertures may be arranged in a helical or partially helical arrangement along a length of the catheter.

Different catheters may have the same configuration of apertures or may differ relative to each other.

The sidewalls of the catheters may define substantially circular apertures although any suitable shape or size of aperture is also envisaged. The sizes of the apertures may vary along the length of the catheter or the apertures may be uniform in size.

In embodiments where a stimulator trocar is not used, a catheter may comprise a nerve stimulator. The catheter nerve stimulator may comprise one or more electrodes positioned in or on the sidewall of the catheter. The one or more electrodes may be positioned adjacent to the distal end of the catheter. The one or more electrodes may be connected to an energy source by an insulated electrode lead. The electrode lead may be embedded in the sidewall of the catheter and extend the full or a partial length of the catheter. Alternatively, the electrode lead may extend through the internal lumen of the catheter. The electrode lead may be of sufficient stiffness to stiffen the catheter to assist in its delivery to a target tissue site.

A catheter may contain one or more flow restrictors, located within the lumen of the catheters. The one or more flow restrictors may control the fluid flow rate through the catheter from the proximal end toward the distal end.

A catheter may exit the exit wound of the patient and be fluidly connected to the reservoir. Multiple catheters may be connected to the reservoir by a suitable connector such as a Y-connector or other multi-limbed connectors in the case of more than two catheters.

Where a common conduit connects to the reservoir, one or more flow restrictors may be provided in at least one of the catheters as a means to control the flow of medicament through the catheter such that the flow rate of medicament in one catheter may differ from the flow rate of medicament in another catheter.

The proximal end of a catheter may be sealable such as to maintain a sterile and enclosed internal environment of the catheter when not fluidly connected to the reservoir.

In a further embodiment of the wearable apparatus described above, the belt may be made a suitably flexible material to encircle a user's body adjacent to the user's skin. Because the belt may, in part, be in contact with the skin of a user, it is desirable that the belt is made of a suitably biocompatible material. Typically the belt is attached around the waist region of a user.

The belt may house one or a number of channels which may either extend through the belt or along a surface of the belt. The channel may include a reservoir channel configured to store a volume of a medicament in liquid form. The reservoir channel may be connected to the pump which, when actuated, draws liquid medicament from the reservoir channel. The channel may also include a delivery channel. The delivery channel may also be connected to the pump. The pump may pump the liquid medicament drawn from the reservoir channel into the delivery channel.

The catheter may be in fluid connection with the delivery channel. The catheter may extend from a connection with the delivery catheter at an access region of the belt. The access region may be at or adjacent to an inner, skin facing surface of the belt.

The belt may include two reservoir channels separated by the pump. Further, the belt may include two delivery channels also separated by the pump. In this embodiment, the pump may draw a medicament from a first reservoir channel and pump this medicament into a first delivery channel. The first delivery channel may be fluidly connected to a first catheter. The pump may also draw a medicament from a second reservoir channel whereupon it pumps this medicament into a second delivery channel. The second delivery channel may be fluidly connected to a second catheter.

The apparatus may further include a housing unit. The housing unit may at least partially surround the belt at or near the access region. The housing unit may include a base. The base may be substantially planar or, alternatively the base may have a slight curvature. The base may be configured for positioning on or adjacent to the user's skin at the access region. The base may also include an aperture which is sized to allow part of the catheter to pass therethrough. The base may further include at least one flange member extending from an edge which defines the aperture. The at least one flange member may be configured to engage or grip a sidewall of part of a catheter which extends through the aperture. The flange member may comprise an inwardly extending skirt around the entire edge defining the aperture. The flange member may be made from a flexible, biocompatible material.

The housing unit may further include an outer protective surface which is spaced from the base by sidewalls. The outer protective surface may cover an outer surface of the belt. The outer protective surface may be made from a relatively harder material than the base.

The base of the housing unit may include an adhesive layer to secure the base to the skin of a patient. The adhesive of the adhesive layer may be made from a suitably biocompatible material.

The catheter typically extends from a proximal end connected to the delivery channel to a distal end which is implanted in the body of the patient. However, the catheter may connect directly to the pump. In this embodiment, the catheter may be received in a channel which is formed on a surface of the belt. Typically the channel is formed on an inner surface of the belt. The catheter may be press-fit into the channel.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

EXAMPLES

A 60 year-old female having previously had rubber banding of haemorrhoids presented with prolapsing large grade 3 haemorrhoids and spontaneous bleeding through clothing. Rubber banding had not controlled the symptoms. A haemorrhoidectomy was scheduled. Two catheters as described herein were implanted into the patient with their distal ends positioned adjacent to the branches of the pudendal nerves on either side of the anus and the surgical removal of the haemorrhoids was carried out. Bilateral infusion of ropivacaine through the catheters was commenced at 2 ml/hr 0.2%. Pain was reported by the patient as 2-4 out of 10 and the patient was observed as very comfortable post operatively. Pain was experienced with each daily bowel action eg 4-8 out of 10, 5-6 out of 10. Oral opioids after bowel actions were introduced.

A 40 year-old male presented with haemorrhoids which were bleeding. Rubber banding treatment had previously been conducted. The haemorrhoids enlarged over the years and he presented with grade 4 haemorrhoids not suitable for any treatment other than haemorrhoidectomy. He deferred the operation until a pain device was available. A haemorrhoidectomy was scheduled. Two catheters as described herein were implanted into the patient with their distal ends positioned adjacent to the branches of the pudendal nerves on either side of the anus. The surgical removal of the haemorrhoids was carried out. Bilateral infusion of ropivacaine through the catheters at 2 ml/hr with 0.2% was commenced and top-up bolus injections after defecation with 10 ml 0.75% ropivacaine each side on days 1, 3 and 5. The patient reported very low-grade pain only, other than the first bowel action. Oral opioids were used once only, after the first bowel action. The catheters were removed on day 7 after surgery.

A 53 year-old female presented with longstanding haemorrhoids, treated by banding several times. The patient had been advised against a haemorrhoidectomy because of pain. She presented with large grade 3 haemorrhoids causing discomfort and itching. A haemorrhoidectomy was scheduled and during the surgery two catheters as described herein were implanted into the patient with their distal ends positioned adjacent to the branches of the pudendal nerves on either side of the anus. The surgical removal of the haemorrhoids was carried out. Bilateral infusion of ropivacaine through the catheters at 2 ml/hr with 0.2%. The patient reported very low levels of pain at 1-2 out of 10 and used only one opioid in first 48 hrs. On day 4 post surgery pain was reported as 8 out of 10 after bowel action. Opioids were used on that day. The catheters were removed on day 6 and the patient only required twice daily long-acting opioids subsequently for two weeks.

DESCRIPTION OF DRAWINGS

By way of example only, embodiments are now described with reference to the accompanying drawings, in which:

FIG. 12b is a cross-sectional view of FIG. 12a;

FIG. 12c is a perspective view of FIG. 12a;

FIG. 13b is a perspective view of the catheter of FIG. 13a;

FIG. 14b is a perspective view of the catheter of FIG. 14a;

FIG. 15b is a perspective view of the catheter of FIG. 15a;

FIG. 16b is a perspective view of the catheter of FIG. 16a;

FIG. 19b is a cross-sectional view of the embodiment shown in FIG. 19a;

FIG. 19d is a perspective view of the embodiment shown in FIG. 19a;

FIG. 20b is a side perspective view of the embodiment shown in FIG. 20a;

FIG. 21b a side perspective view of the embodiment shown in FIG. 21a;

FIG. 24a is a perspective view of the various parts of a casing of the present invention;

FIG. 24b shows the casing of FIG. 24a, held in a pouch on a patient's body;

DETAILED DESCRIPTION OF EXEMPLARY EMBODIMENTS

A wearable apparatus according to an exemplary embodiment of the present disclosure is illustrated generally as 10 in the accompanying drawings. The wearable apparatus 10 includes a belt 11, pump 12, catheters 13*a*, 13*b*, and housing units 14*a*, 14*b*. As discussed in more detail below, the belt 11 is attachable to a patient around their waist and catheters 13*a*, 13*b* are configured to be implanted in the patient with distal ends 31*a* and 31*b* at or adjacent to a right and left pudendal nerve respectively to deliver pain relief medicament directly to the nerves.

Catheter 13*a* extends from a proximal end 30*a* to a distal end 31*a* and has a sidewall 32*a* which defines an internal lumen 34*a*. Apertures 35*a* provide a fluid flow path from the internal lumen 34*a* to the outside of catheter 13*a*. Catheter 13*b* extends from a proximal end 30*b* to a distal end 31*b* and has a sidewall 32*b* which defines an internal lumen 34*b*. Apertures 35*b* provide a fluid flow path from the internal lumen 34*b* to the outside of catheter 13*b*.

In the depicted embodiments, both proximal ends 30*a*, 30*b* of catheters 13*a*, 13*b*, respectively, are in fluid connection with pump 12 such that the pump 12 pumps a medicament into both catheters 13*a*, 13*b*. The medicament may be pumped in unison, delivering medicament to both catheters 13*a* and 13*b* at substantially the same time. Alternatively, the pump may alternate between delivery of medicament to catheter 13*a* and catheter 13*b* at different time periods.

Figure 1A:
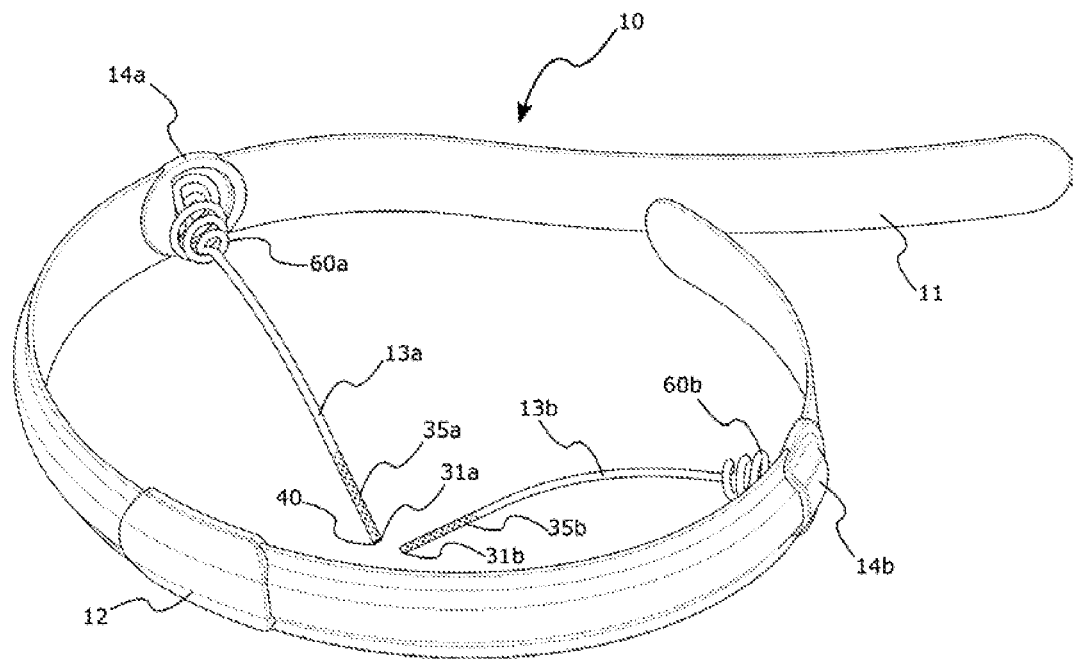
FIGS. 1A and 1B show perspective views of a wearable apparatus for delivery of a medicament device according to an embodiment of the present disclosure.
Figure 1B:
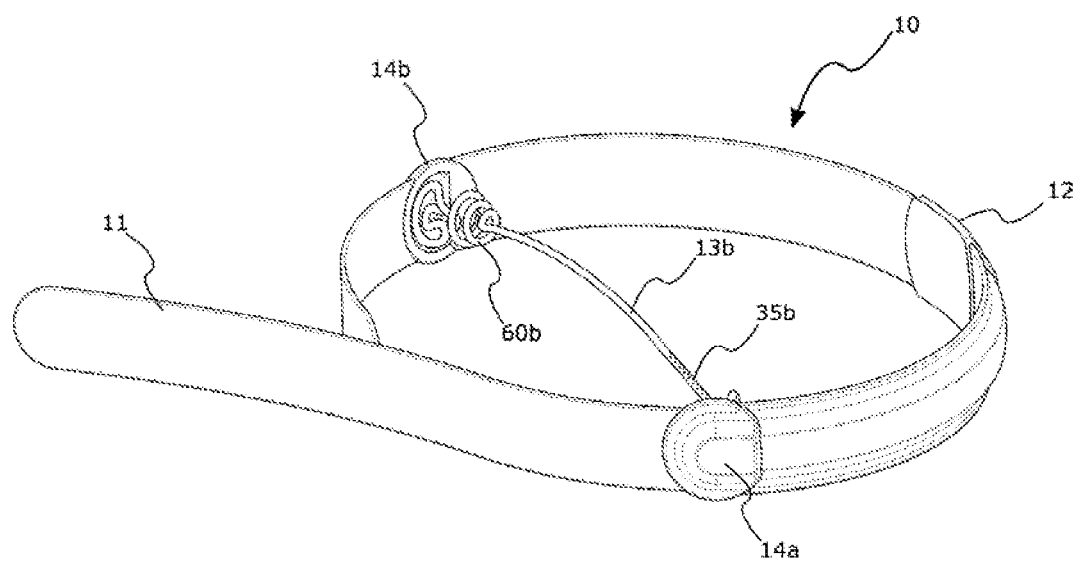
Figure 2A:
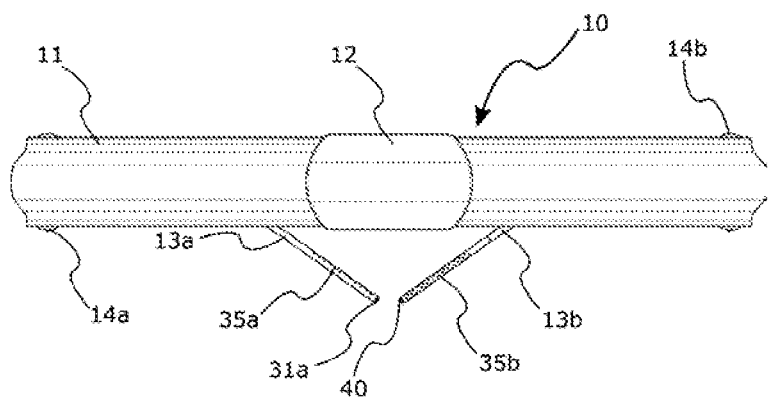
FIGS. 2A, 2B, and 2C shows front, top, and side views, respectively, of the wearable apparatus of FIGS. 1A and 1B.
Figure 2B:
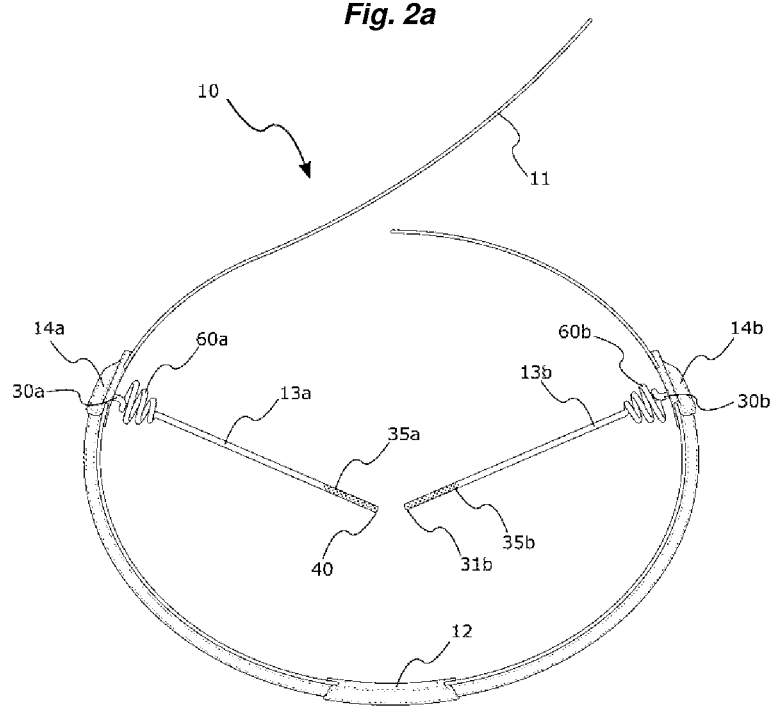
Figure 2C:
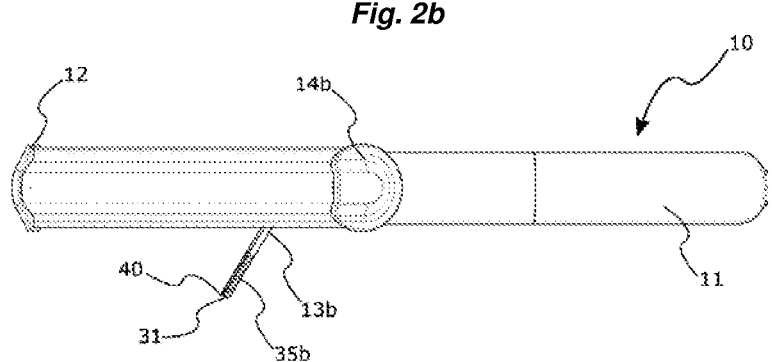
Figure 3:
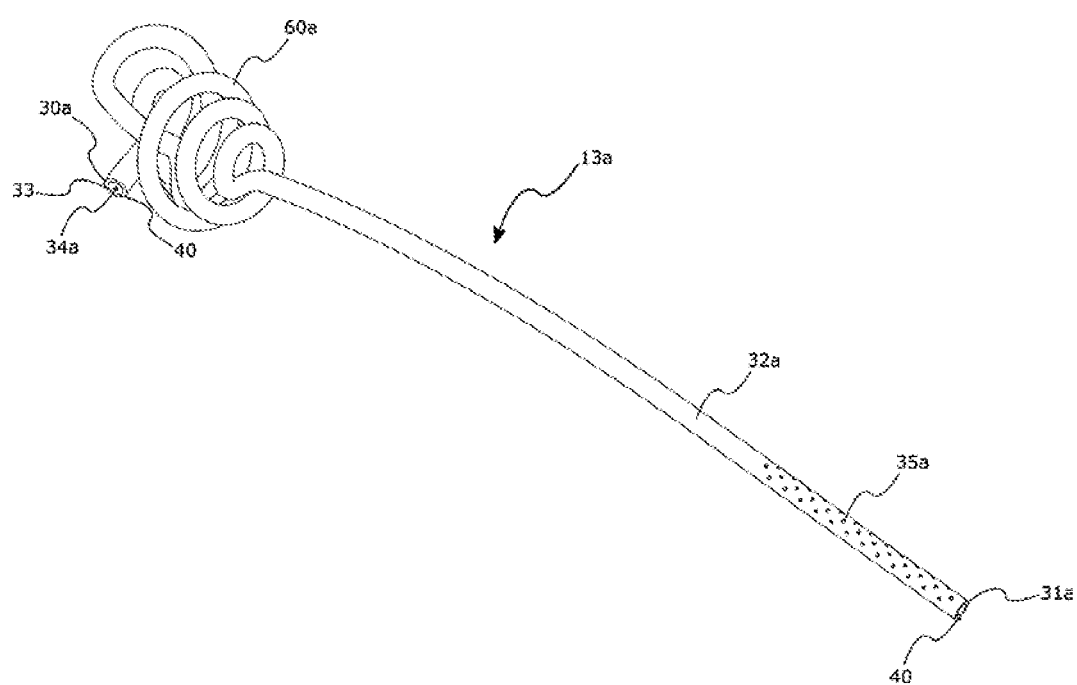
FIG. 3 shows a perspective view of a catheter of the wearable apparatus of FIGS. 1A and 1B.

FIG. 3 depicts a view of one of the catheters 13*a*. The same features may equally apply to catheter 13*b*. Catheter 13*a* extends from proximal end 30*a* to distal end 31*a*. Adjacent distal end 31*a*, the catheter sidewall has a plurality of apertures as described above for the delivery of a medicament. A coiled region 60*a* of catheter 13*a* extends from proximal end 30*a*. Coiled region 60*a* is configured such that it is positioned beneath the skin of the patient when the catheter 13*a* is implanted. The coiled structure acts as a strain relief and prevents pulling or tugging at the wound site which could open the wound and cause discomfort for the patient and an increased risk of infection. Typically, the coiled region 60*a* extends a length of the catheter 13*a* such that it sits in the fatty layer beneath the skin of the patient. Catheter 13*b* also has a coiled region 60*b* as depicted in, for example, in FIGS. 1A and 2B.

Coiled regions 60*a* and 60*b* may include a shape memory material such that when inserted in the body, said regions adopt the coiled configuration.

Figure 4:
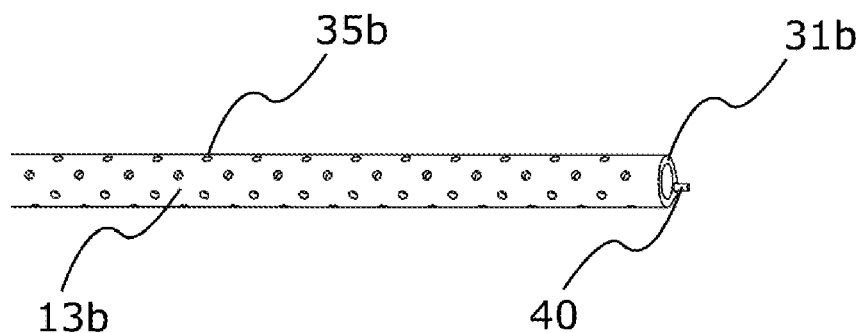
FIG. 4 shows a view of a distal end of the catheter of FIG. 3.

The distal end 31*b* of catheter 13*b* is shown in more detail in FIG. 4. The same features are to be understood to also apply to catheter 13*a* and catheter 13*b* has been selected purely for illustrative purposes. In this embodiment catheter 13*b* comprises a distally extending electrode 40. The electrode 40 is connected proximally to an electrical source (not shown). The electrode 40 is used during surgery to achieve accurate positioning of catheters 13*a* and 13*b* adjacent to respective pudendal nerves. By stimulating the tissue adjacent the nerve with the electrode, the surgeon may view twitching of the muscles adjacent to the anus thus establishing that the distal ends of the catheters 13*a* or 13*b* are properly positioned.

Figure 5:
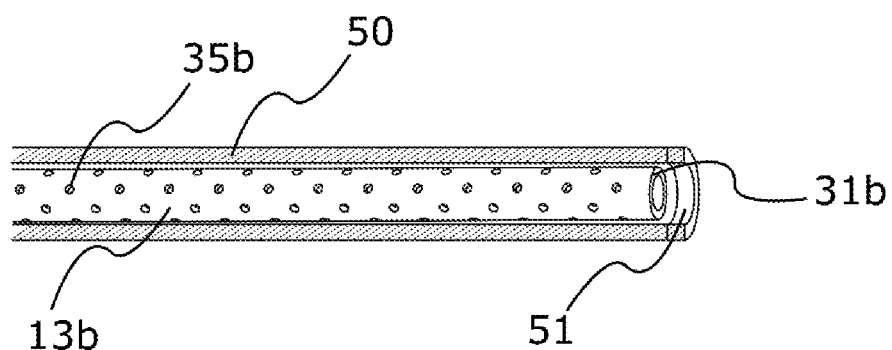
FIG. 5 shows a view of a distal end of the catheter of a wearable apparatus according to another embodiment of the present disclosure where the catheter includes a trocar.

Referring to FIG. 5, in another embodiment of the present disclosure, a delivery trocar 50 may substantially surround catheter 13*b*. Trocar 50 is of sufficient rigidity to guide the catheter 13*b* through the tissue to a desired nerve site. The trocar 50 in this embodiment includes an electrode 51 at its distal end. Similarly, catheter 13*a* may also be guided by a trocar 50. Once guided by trocar 50 to the desired site in the patient's body, the trocar is withdrawn to leave the catheter 13*a* or 13*b* in situ.

Figure 6:
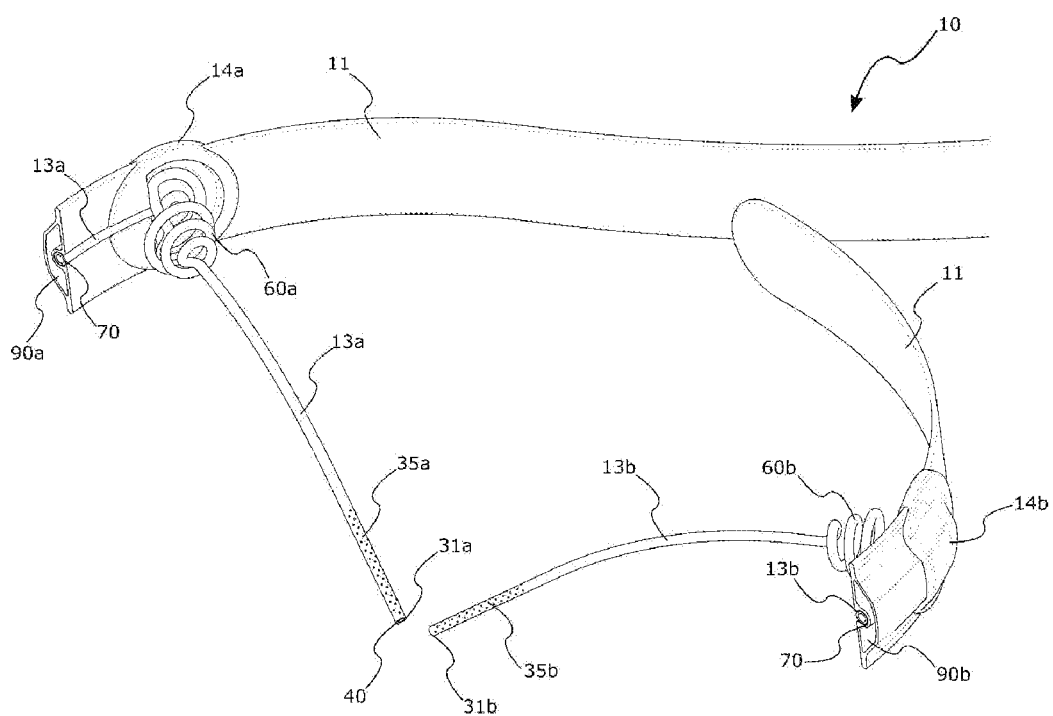
FIG. 6 shows a perspective view depicting a cross sectional cut away of the belt of the wearable apparatus of FIGS. 1A and 1B.

Once the catheters 13*a* and 13*b* are positioned and the distal ends 31*a* and 31*b* respectively are adjacent to the desired nerve tissue, the proximal end of the two catheters 13*a* and 13*b* may be connected either directly or indirectly to pump 12. In this regard, FIG. 6 shows an embodiment wherein catheter 13*a* is aligned with a trench 70 on an inner surface of belt 11. The catheter is typically press fit into the trench 70 which runs along a length of the inner surface of belt 11 and terminates adjacent pump 12 to allow catheter 13*a* to be directly connected to pump 12.

In a further embodiment, the catheters 13*a*, 13*b* do not connect directly with pump 12 but instead are connected to respective delivery channels 80*a*, 80*b* which extend internally within belt 11.

Figure 7:
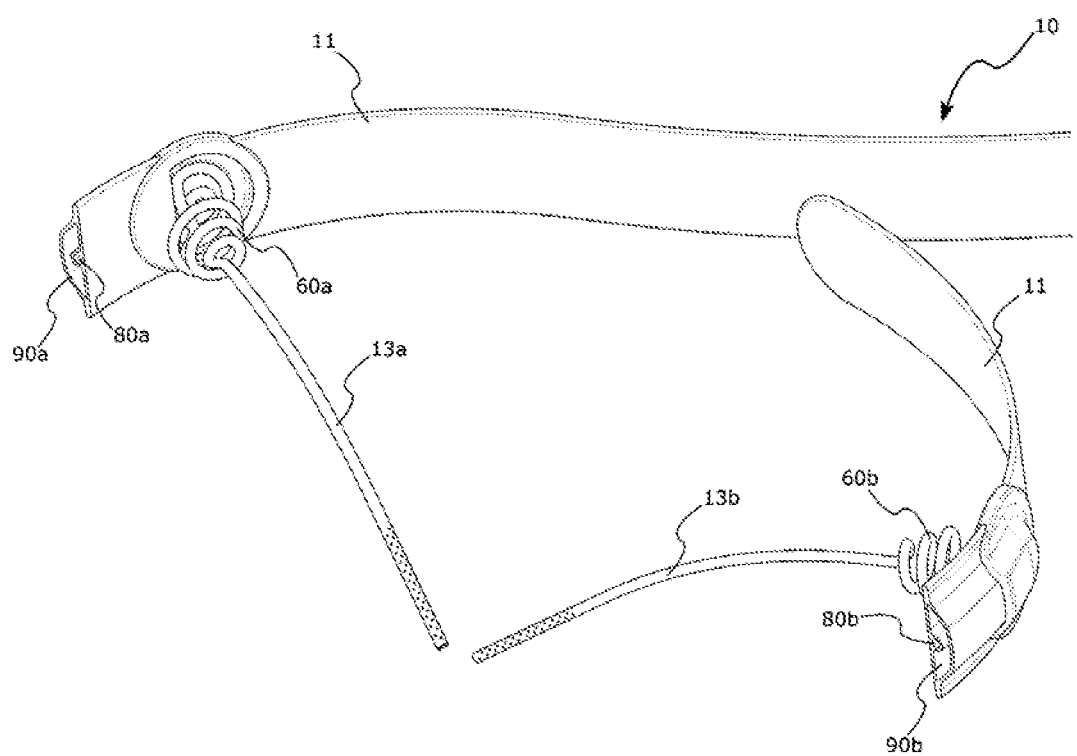
FIG. 7 shows a perspective view depicting a cross sectional cut away of the belt of a further embodiment of the wearable apparatus of FIGS. 1A and 1B.
Figure 8:
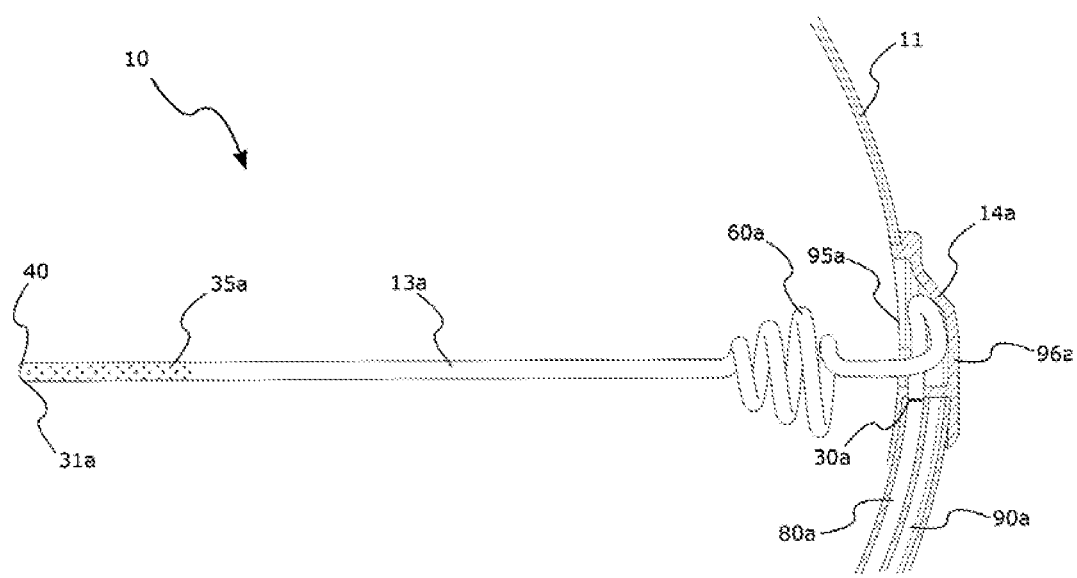
FIG. 8 shows a top cross-sectional view of part of the wearable apparatus of FIGS. 1A and 1B.

In the embodiment shown in FIG. 7, the proximal ends 30*a* of catheter 13*a* and 30*b* of catheter 13*b* extend from a wound site on the skin of a patient and into respective housings 14*a* and 14*b*. As shown more clearly in FIG. 8, proximal end 30*a* of catheter 13*a* connects with a delivery channel 80*a* within housing 14*a*. Although not shown, delivery channel 80*a* extends through the belt and connects with pump 12. Similarly, proximal end 30*b* of catheter 13*b* connects with a delivery channel 80*b* within housing 14*b*. Delivery channel 80*b* extends through the belt 11 on an opposite side of the belt and connects with pump 12.

Pump 12 may be positioned either at the front of the belt such that it sits adjacent to the navel region of a wearer or at the rear of belt 11 to sit adjacent the small of the back of a wearer. Pump 12 may draw medicament from a single reservoir or it may draw from multiple reservoirs. In FIGS. 6 and 7, two separate reservoirs 90*a* and 90*b* are depicted. In FIG. 6 catheters 13*a* and 13*b* extend along a trench 70 on a surface of belt 12 and connect directly to the pump 12. Pump 12 draws medicament from reservoir 90*a* and pumps this medicament to catheter 13*a*. Pump 12 also draws medicament held in reservoir 90*b* and pumps this medicament into catheter 13*b*.

In the embodiment depicted in FIG. 7, pump 12 draws medicament from reservoir 90*a* and pumps this medicament into delivery channel 80*a* for delivery to catheter 13*a*. Pump 12 also draws medicament from reservoir 90*b* and pumps this medicament into delivery channel 80*b* for delivery to catheter 13*b*.

Housing 14*a* has a base 95*a* and an outer surface 96*a*. Base 95*a* may include an adhesive surface to secure the housing over the wound site of a patient. The housing has a height sufficient to allow part of the proximal region of catheters 13*a*, 13*b* to turn at an angle and connect with a delivery channel without the risk of the catheters kinking. Housing 14*b* may have the same features as housing 14*a*.

Turning to the exemplary method shown in FIGS. 9*a* to 9*h*, the drawings depict a patient in position for an operation to surgically remove their haemorrhoids. The patient is typically placed on the operating table under general anaesthetic with muscle relaxation in the depicted modified lithotomy position. The perineum, pelvic area and thighs are prepared in a sterile field using a solution of iodine and alcohol. An iodine-impregnated adhesive mat 500 is placed vertically from the pubis to cover the vagina/scrotum and the anal region. This area is kept sealed until the catheters 100 and 200 are implanted in the desired position. The adhesive mat 500 comprises a first frangible region 501 with serrations in the mat allowing a small area of the mat (here shown as a square but could be any shape) to be torn off, for access to the skin beneath. The surgeon makes a stab incision A at this region and then removes a similarly shaped frangible region 502 of mat 500 and makes a second stab incision B at this region. A lateral stab incision is made at point C.

Trocar 300 comprises an elongate body 301 extending from handle 302 to tip 303. The tip 303 may be shaped to separate tissue in the patient. The trocar 300 may also have a hook feature 304 adjacent tip 303.

Catheter 100 extends from a proximal end 101 to a distal end 102 and has a sidewall 103 which defines an internal lumen 104. One or more apertures 105 are formed in the sidewall adjacent distal end 102 to allow for fluid in the internal lumen to pass into the surrounding tissue. Distal end 102 may be further modified to have a trocar receiving opening 106. The apertures 105 may be positioned proximal to the trocar receiving opening 106 and the internal lumen 104 may terminate proximal to the trocar receiving opening 106 to prevent medicament flowing at an uncontrolled flow rate out of the larger opening 106 rather than through the apertures 105. In an alternative embodiment, the proximal end of catheter 100 has the trocar receiving opening with the apertures positioned at the distal end 102.

Figure 9A:
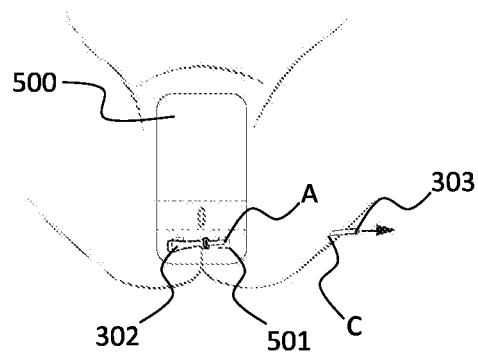
FIGS. 9a to 9h show the steps of one exemplary embodiment of a method of implanting two infusions catheters in a patient.
Figure 9B:
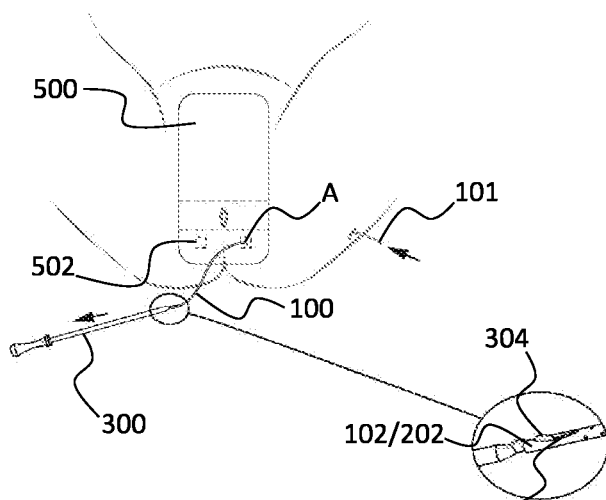

Trocar 300 is typically between 30 cm and 40 cm in length and may also have a surrounding sheath (not shown in the drawings). The trocar 300 is passed subcutaneously from incision A to incision C as shown in FIG. 9*a*. At incision C the hook feature 304 is hooked into a receiving aperture 106 at distal end 102 of catheter 100 and the trocar withdrawn back subcutaneously to incision A until distal end 102 of catheter 100 is drawn through incision B. A length of catheter 100 at distal end 102 extends through incision A and a length of catheter 100 adjacent proximal end 101 extends through incision C as depicted in FIG. 9*b*.

Catheter 200 extends from a proximal end 201 to a distal end 202 and has a sidewall 203 which defines an internal lumen 204. One or more apertures 205 are formed in the sidewall adjacent distal end 202 to allow for fluid in the internal lumen to pass out and into the surrounding tissue. Distal end 202 may be further modified to have a trocar receiving opening 206. The apertures 205 may be positioned proximal to the trocar receiving opening and the internal lumen 204 may terminate proximal to the trocar receiving opening 206 to prevent medicament flowing at an uncontrolled flow rate out of the larger opening 206 rather than through the apertures 205.

Figure 9C:
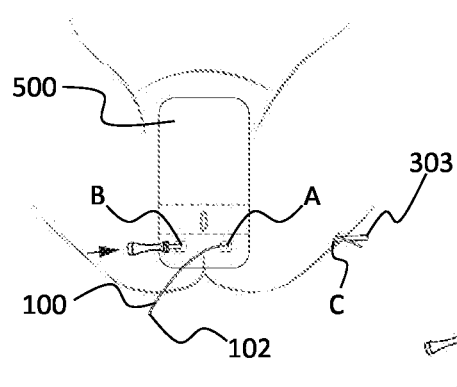
Figure 9D:
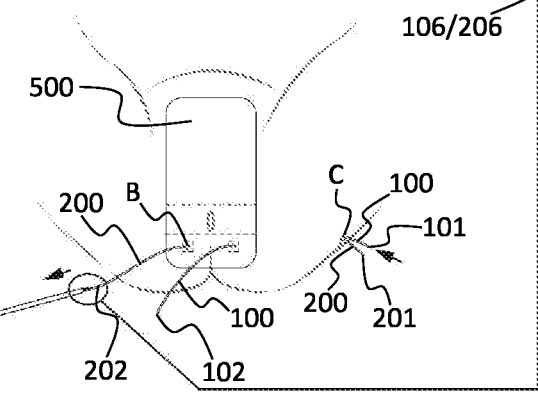

Trocar 300 is passed subcutaneously from incision B to incision C as shown in FIG. 9*c*. This step requires passing the trocar 300 through the thicker central midline tissue to create a path for catheter 200. At incision C the hook feature 304 of the trocar is hooked into receiving aperture 206 of catheter 200 and the trocar 300 withdrawn back subcutaneously to incision B until catheter 200 is drawn through incision B. A length of catheter 200 at distal end 202 extends through incision A and a length of catheter 200 adjacent proximal end 201 extends through incision C as can be seen in FIG. 9*d*.

A nerve stimulating trocar 400 comprises an elongate solid body 401 having a proximal region 402, a distal region 403 terminating in a tip 404. The nerve stimulating trocar 400 further includes an intermediate region 405 between the proximal 402 and distal regions 403.

Figure 19A:
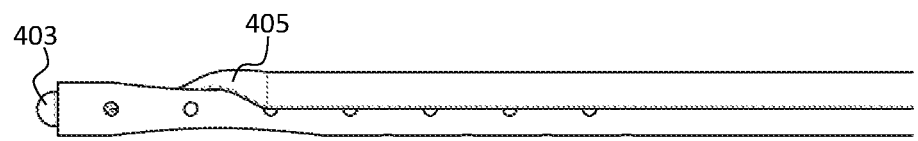
FIG. 19a is a side view of an embodiment of a nerve stimulating trocar inserted into part of a catheter of the present disclosure.
Figure 19B:
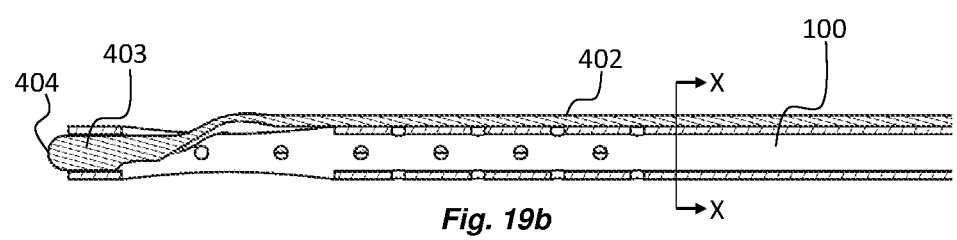

Nerve stimulating trocar 400 acts to both deliver a stimulation to a nerve in the patient and also to provide a relatively rigid structure to deliver the catheters 100 or 200 to the desired location in the body. The nerve stimulating trocar 400 can have one or more nerve stimulating electrodes 410 at, or proximal to tip 404. Alternatively, the electrode 410 may extend beyond tip 404 as shown in, for example, FIGS. 19*a* and 19*b*.

The nerve stimulating assembly may comprise an electrically conductive lead 411 that is substantially embedded in the trocar and extends along a length of the trocar 400. Electrode lead 411 connects to an energy source (not shown). The electrode 410 in this embodiment is formed where lead 411 extends beyond tip 404 of trocar 400.

Figure 20A:
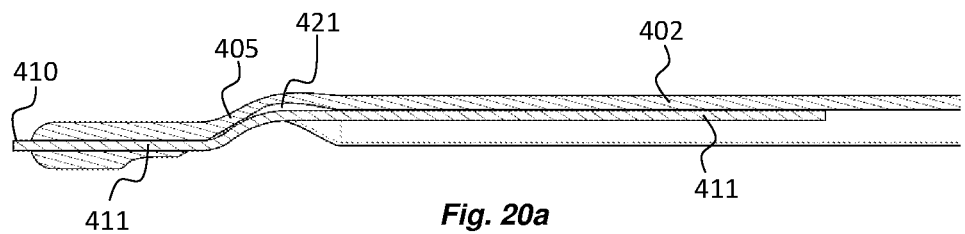
FIG. 20a is a side sectional view of an embodiment of a nerve stimulating trocar.
Figure 20B:
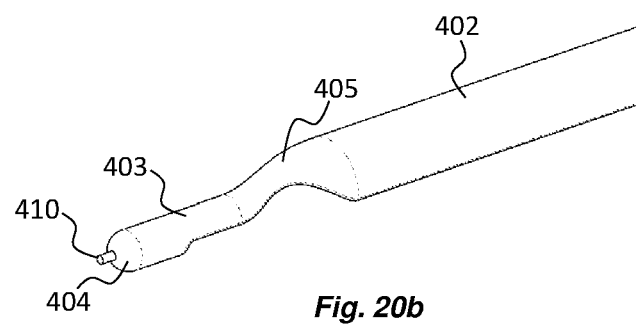
Figure 21A:
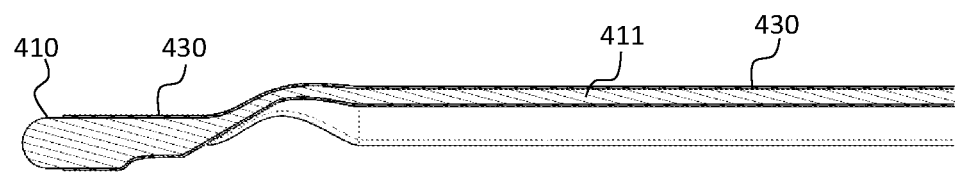
FIG. 21a is a side sectional view of another embodiment of a nerve stimulating trocar.
Figure 21B:
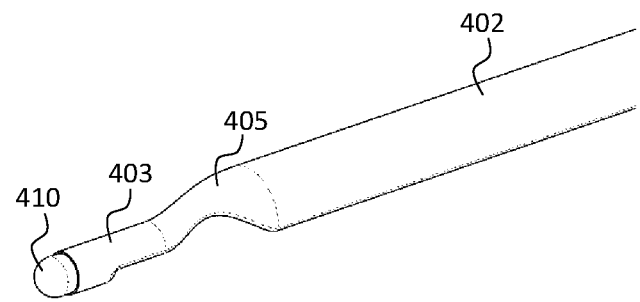
Figure 22A:
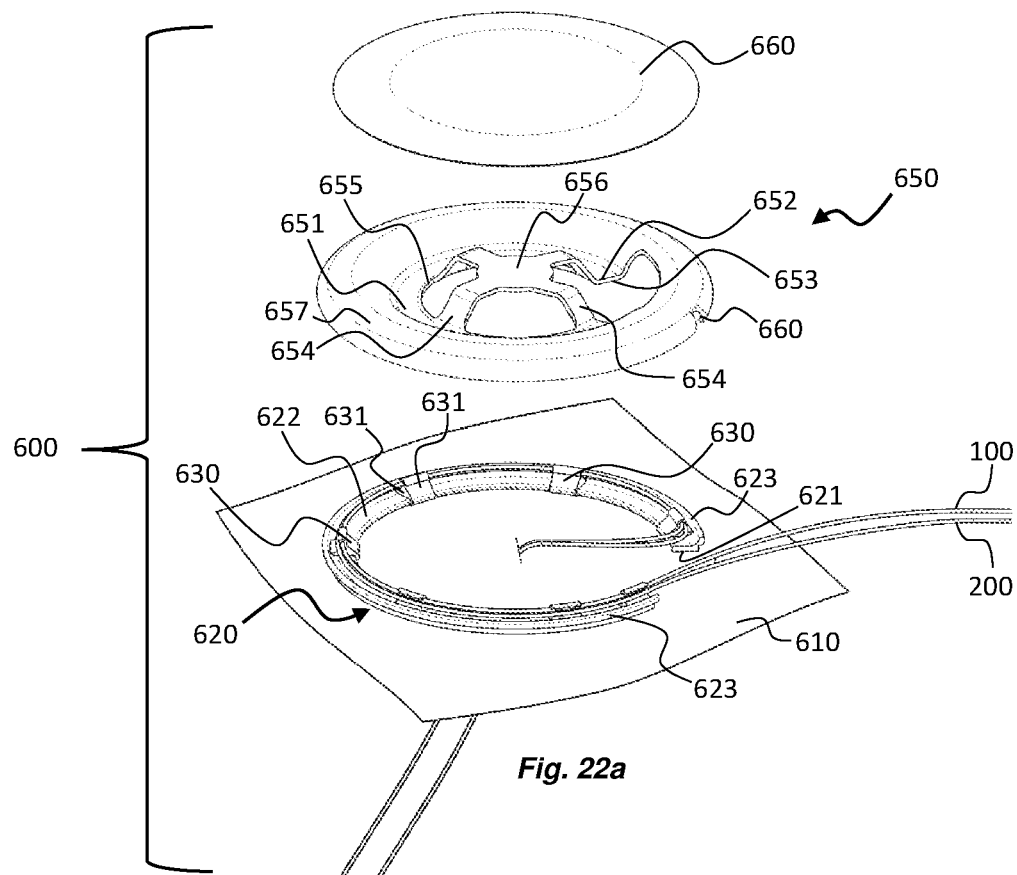
FIG. 22a is a perspective view of the parts making up a retainer in one embodiment.
Figure 22B:
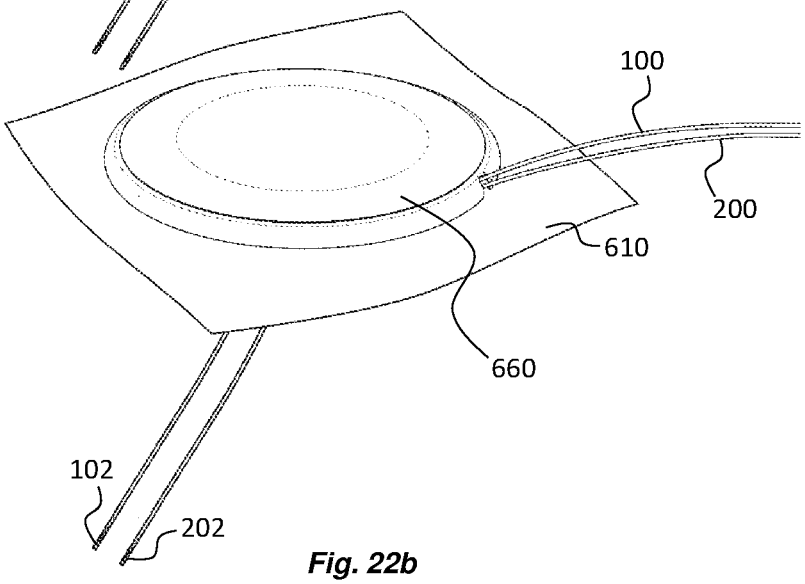
FIG. 22b depicts the retainer with a cover over the parts.

In an alternative embodiment, as shown in FIG. 20*a*, the electrode lead 411 is insulated with non-conductive insulator 430 and extends along an external surface of trocar 400. The electrode 410 comprises a non-insulated part of the lead 411.

Figure 19C:
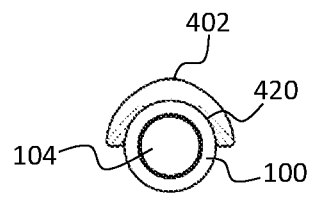
FIG. 19c is a cross-sectional view through X-X of FIG. 19b.
Figure 19D:
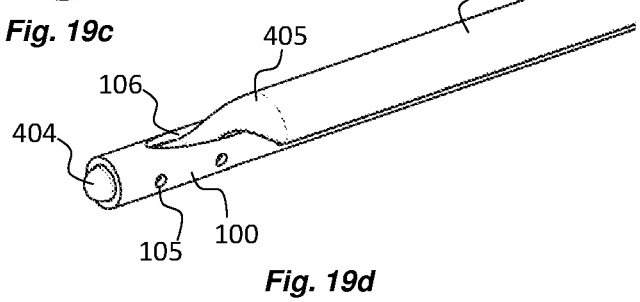

Nerve stimulating trocar 400 is configured to align with an outer surface of catheter 100 or 200 and as such typically has an inner curved surface 420 as shown in FIG. 19*c*.

Intermediate region 405 of trocar 400 forms a bend in body 401 such that a main axis of the proximal region 402 is offset and substantially parallel to a main axis of the distal region 403.

Tip 404 of trocar 400 is inserted into opening 106 of catheter 100 or opening 206 of catheter 200 such that it extends beyond distal ends 102 or 202 respectively. Distal region 403 sits recessed within the openings 106 or 206.

Figure 9E:
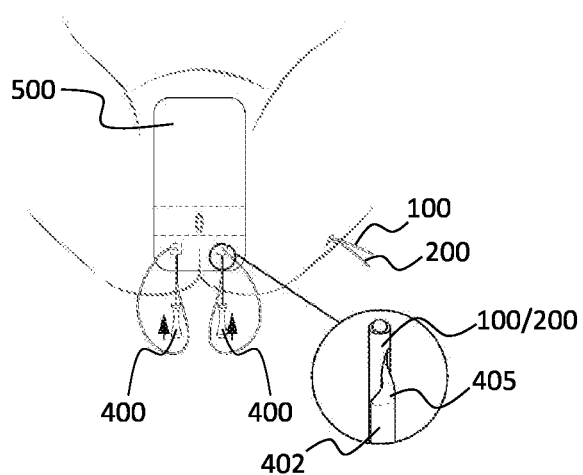

Referring to FIG. 9*e*, once the distal region 403 is in position within opening 106, trocar 400 and catheter 100 are passed through incision A and angled to pass deeply into the tissue until at a region where the target nerve branches e.g. the pudendal nerve branches are located.

In another exemplary embodiment shown in FIGS. 14*a*, 14*b*, 16*a* and 16*b*, the catheters 100 and 200 include an electrically conductive lead 111 and 211 that is either embedded in the sidewall of the catheters or passes through the internal lumina 104/105. Electrode lead 111 connects to an energy source (not shown) and the electrode 110 in this embodiment is formed where lead 111 extends beyond distal end 102 of catheter 100. Similarly, electrode lead 211 connects to an energy source (not shown) and the electrode 210 in this embodiment is formed where lead 211 extends beyond distal end 202 of catheter 200.

In the embodiments where the electrodes 100 and 200 have an electrode, they may still be used with a modified trocar similar to the nerve stimulating trocar 400 but without the electrode 410 and electrical lead 411.

The energy source is then activated. In one embodiment, the energy source is an electrical energy source which delivers an electrical stimulus to electrode 410. The electrical stimulus is typically between 3-5 m Amp and at a frequency of between 0.5-1.0 Hz. The surgeon watches for contraction of the external sphincter of the anus at a cycle rate as set. The surgeon may move the trocar 400 and catheter 100 until this contraction is observed. This indicates to the surgeon that the one or more electrodes 410 are adjacent to the branches of the pudendal nerve and that the distal end 102 of the catheter is thus in a position to infuse medicament from apertures 105 to the branches of the pudendal nerve.

The next step is to disengage trocar 400 from catheter 100, careful not to dislodge distal end 102 from its position adjacent to the pudendal nerve branches. Trocar 400 is withdrawn from the patient through incision A.

The process is repeated through incision B using trocar 400 and catheter 200 as also shown in FIG. 9*e*.

Figure 9F:
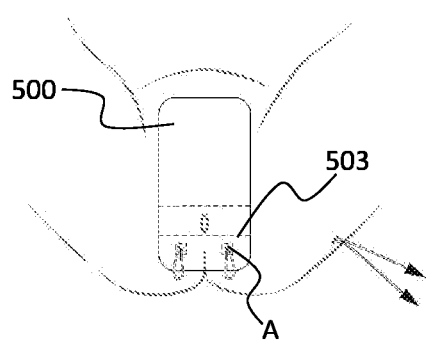

The proximal ends 101 and 201 of catheters 100 and 200 are then pulled in the direction shown by the arrows in FIG. 9*f* to pull the excess of each catheter at incisions A and B subcutaneously. Again, the catheters are not pulled such as to cause any dislodgement of the positioning of the distal ends 102 and 202 adjacent to the branches of the pudendal nerves.

The surgeon removes a portion of the adhesive mat 500 by tearing along frangible line 503. The incisions A and B are then sealed.

The lengths of catheter that exit incision C are retained by retainer 600. Retainer 600 has several parts including an adhesive film 610 which adheres to the skin over incision C. Adhesive film 610 has a central aperture, slit or flap to allow the passage of catheters 100 and 200 from incision C therethrough.

Retainer 600 further includes a retainer body 620 which comprises a partially circular structure having a relatively planar base surface 621 configured to sit on the adhesive film 610 and an opposed guide surface 622 to receive a length of the first catheter 100 and/or the second catheter 200. The guide surface 622 may be curved and terminate in an outer rim 623. A series of clips 630 retain the catheters 100 and/or 200 to the guide surface 622. The clips 630 may be formed integrally with the retainer body 620 or may be a separate structure which clip onto the retainer body 620. The clips 630 include jaw members 631 which together form a tunnel through which one or more of the catheters 100 or 200 may pass. The clips 630 may be made from a resiliently flexible material and the jaw members may be moveable between an open configuration to allow the catheter to be laid along the guide surface 622 and a closed configuration to form the tunnel to secure the catheters 100 and 200. The jaw members 631 may be biased to adopt the closed configuration.

Retainer 600 further includes housing 650. Housing 650 comprises a substantially circular base 651 having an outer facing surface 652 and a substantially flat inner surface 653. An outer rim 657 extends peripherally from circular base 651 and terminates in a lip 660. Lip 660 attaches to part of rim 623 of retainer body 620 to secure the two parts together. A plurality of arms 654 extend centrally from an inner edge 655 of circular base 651. Arms 654 terminate in a central body 656. Central body 656 is configured to sit directly over incision C where the catheters 100/200 exit the patient's body to provide extra protection from any external forces to this area.

Retainer 600 also includes a cover 660 configured to clip onto the housing 650.

Retainer 600 both protects the wound of the patient and prevents strain on catheters 100/200 which could cause them to be pulled out of the incision C.

The retainer body 620 is a split ring structure as shown and therefore it can be oriented such as to direct the catheters 100 and/or 200 in a desired direction as they exit the retainer body 620. The proximal ends 101 and 201 of the catheters are ultimately connected to a medicament reservoir 700 which can be carried in a pouch 800 or like device anywhere on the patient's body. The patient may choose their preference for the location of pouch 800 prior to surgery and the retainer body 620 oriented accordingly such that the catheters 100 and/or 200 are directed towards the pouch 800.

Figure 23A:
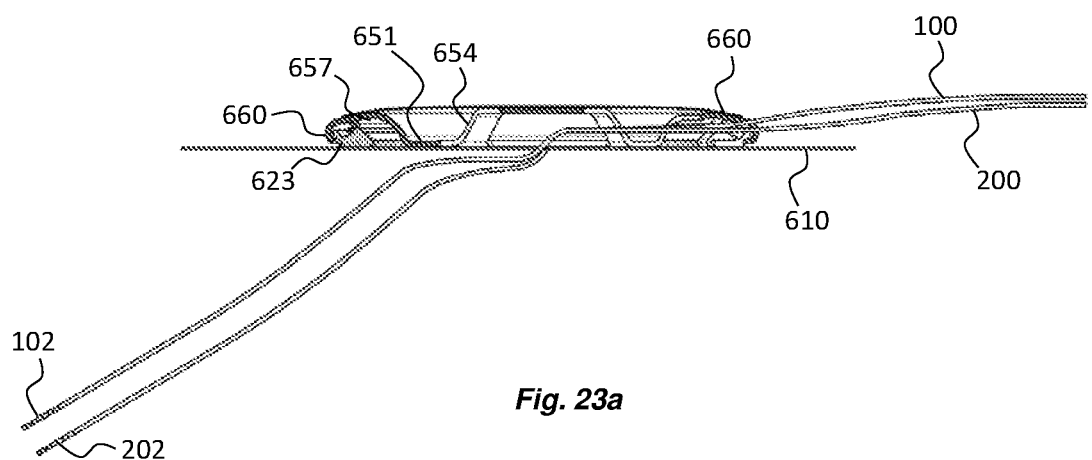
FIG. 23a is a cross sectional view of the retainer and catheters of the present disclosure.
Figure 23B:
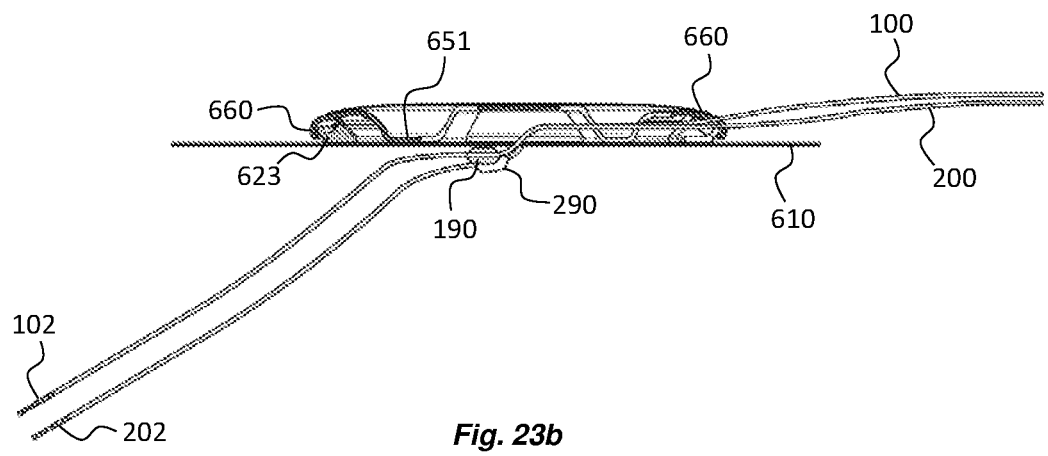
FIG. 23b is a cross sectional view of the retainer wherein the catheters wherein the catheters comprise balloons.
Figure 24C:
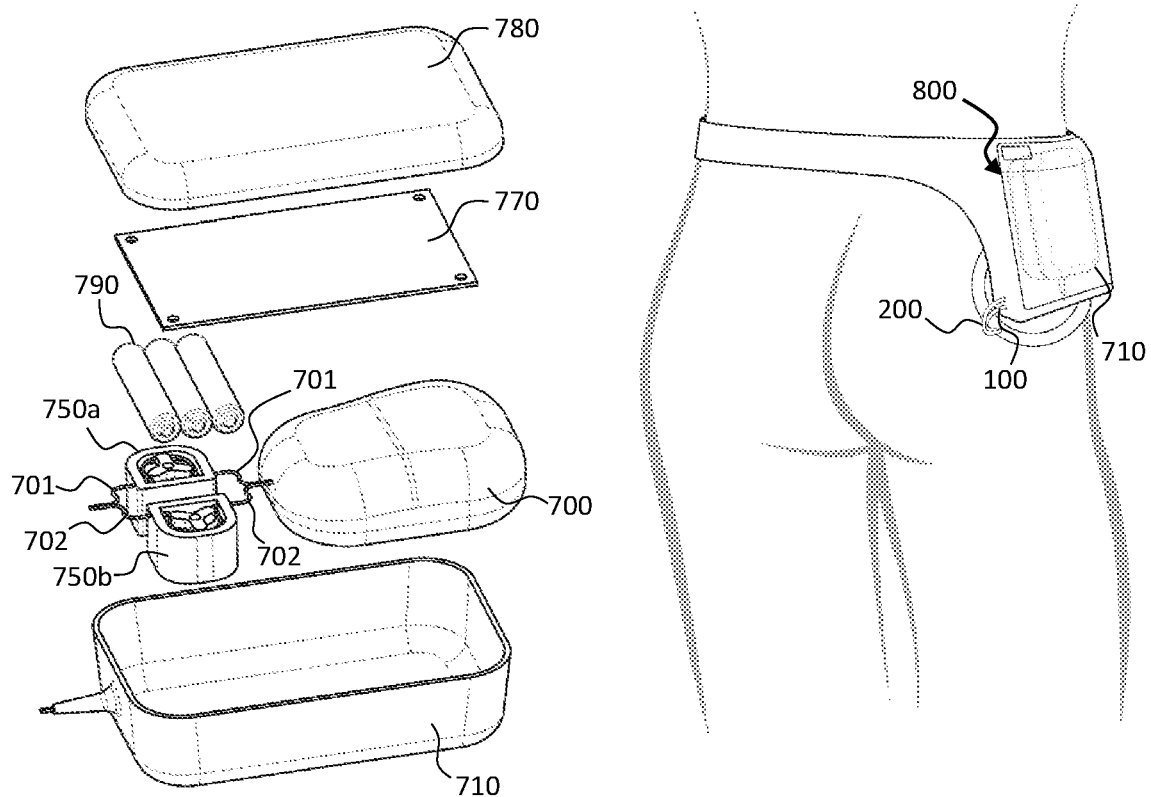
FIG. 24c is a sectional view of the casing.
Figure 24C:
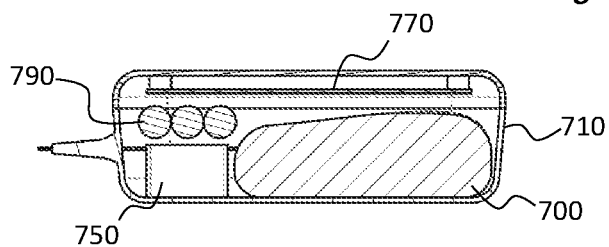

Before connecting the catheters 100/200 to a medicament reservoir 700, balloon members 190 and 290 may be threaded over proximal ends 101 and 201 of respective catheters 100 and 200 and inserted though incision C to a location just beneath the skin as shown in FIG. 23b. The balloon members 190 and 290 are typically inserted into the skin in a deflated configuration and once in position they are inflated using a flexible inflation tube (not shown). The balloons 190 and 290 act to secure the catheters 100/200 and prevent dislodgement.

Casing 710 houses medicament reservoir 700 and pump 750. The medicament reservoir 700 is connected to separate pumping members 750a and 750b of pump 750 by two tubes 701 and 702. In the example shown, pump members 750a and 750b are peristaltic pumps but other pump means are envisaged. In the depicted embodiment, tube 701 is fed through and extends from pumping member 750a. Likewise, tube 702 is fed through and extends from pumping member 750b.

The two tubes 701 and 702 extend through an opening in 710 and are connectable to the proximal ends of catheters 100 and 200 respectively.

Having separate pumping members 750a and 750b for each catheter has the advantage of a greater control on flow to each target tissue site. Catheter 200 is longer than catheter 100 (because it travels further in the body) so requires a different pumping programme to ensure that the same amount, and at the same rate, of medicament is delivered to the nerve branches relative to catheter 100.

A protective plate 770 covers the pump 750 and the medicament reservoir 700 and the power supply such as batteries 790. Casing 710 also has a removable lid 780 which may be readily opened to allow replacement of the medicament reservoir 700 as needed.

Figure 9G:
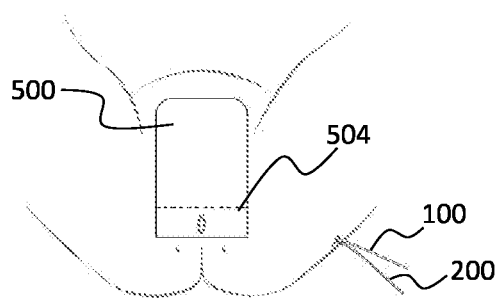
Figure 9H:
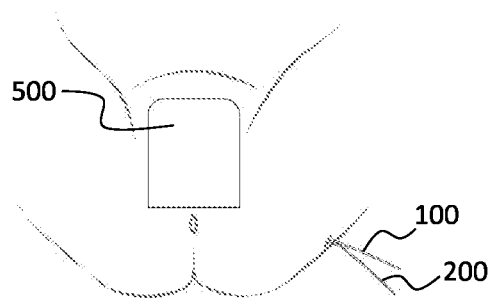
Figure 10:
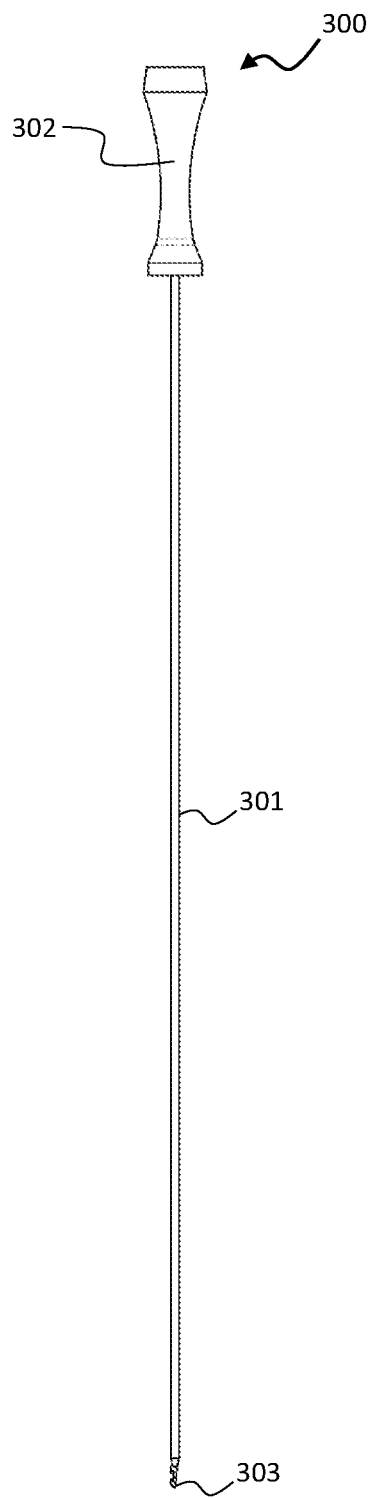
FIG. 10 is a side view of a trocar used in the method shown in FIGS. 9a to 9h.
Figure 11A:
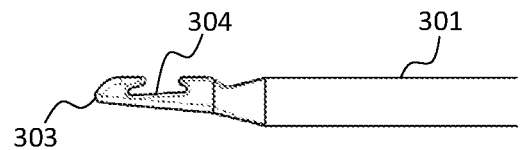
FIG. 11a is a side view of a hook feature of the trocar of FIG. 10.
Figure 11B:
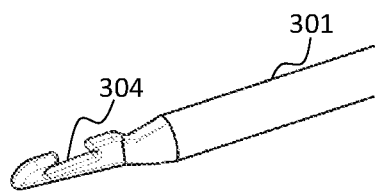
FIG. 11b is a perspective view of the hook feature of the trocar of FIG. 10.
Figure 12A:
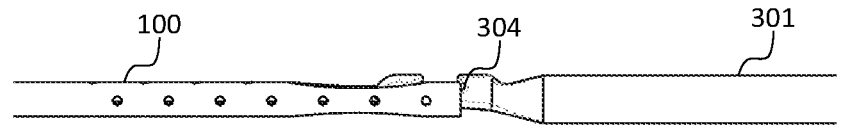
FIG. 12a is a side view showing the engagement of the hook feature of the trocar of FIG. 10 engaging with a catheter of the present disclosure.
Figure 12B:
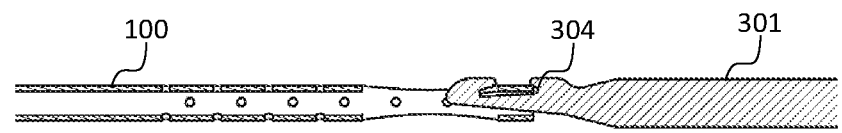
Figure 12C:
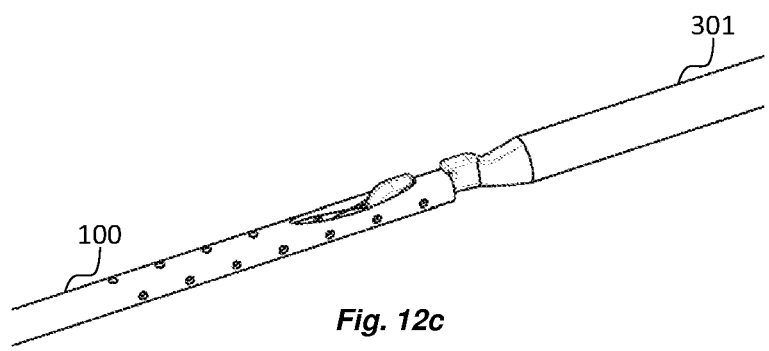
Figure 13A:
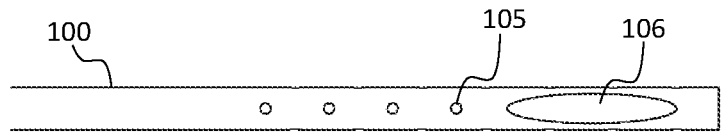
FIG. 13a is a top plan view of an embodiment of a catheter of the present disclosure.
Figure 13B:
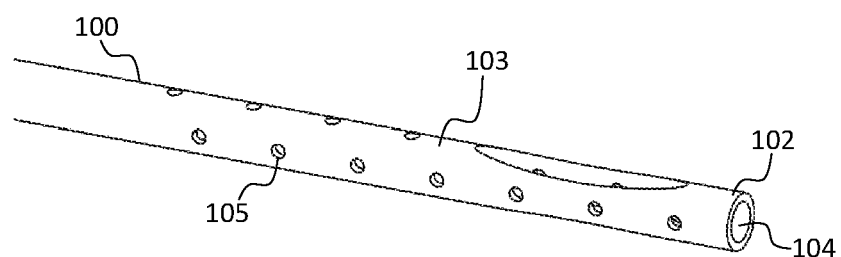
Figure 14A:
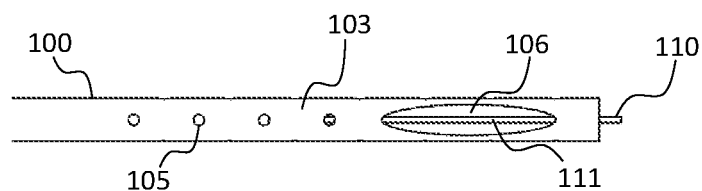
FIG. 14a is a top plan view of a further embodiment of a catheter of the present disclosure.
Figure 14B:
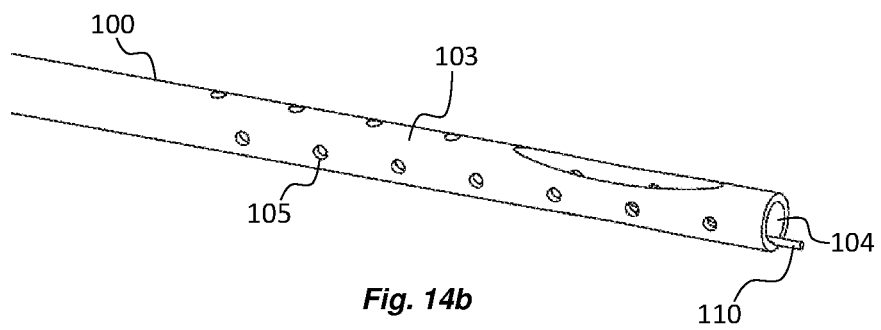
Figure 15A:
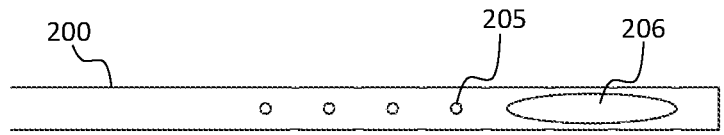
FIG. 15a is a top plan view of an embodiment of another catheter of the present disclosure.
Figure 15B:
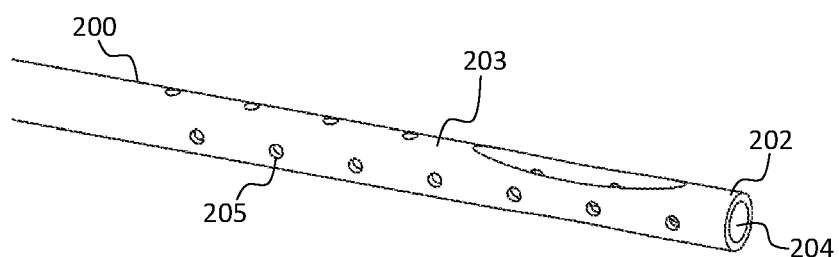
Figure 16A:
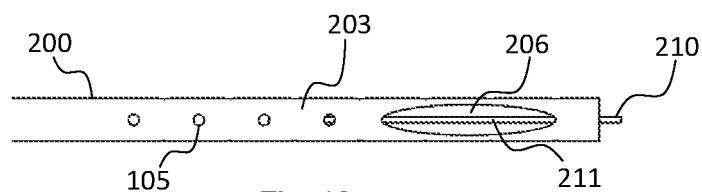
FIG. 16a is a top plan view of a further embodiment of a catheter of the present disclosure.
Figure 16B:
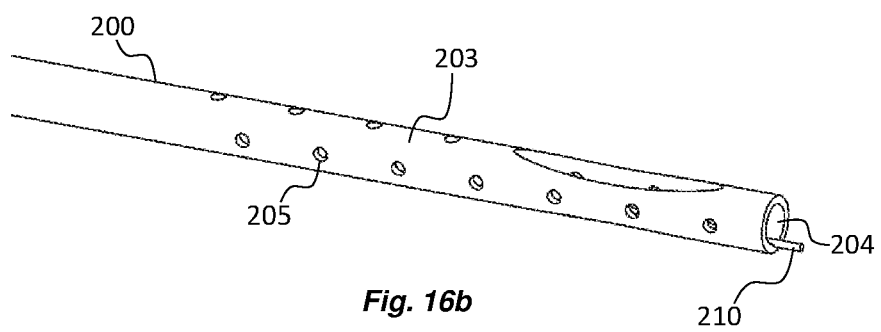
Figure 17:
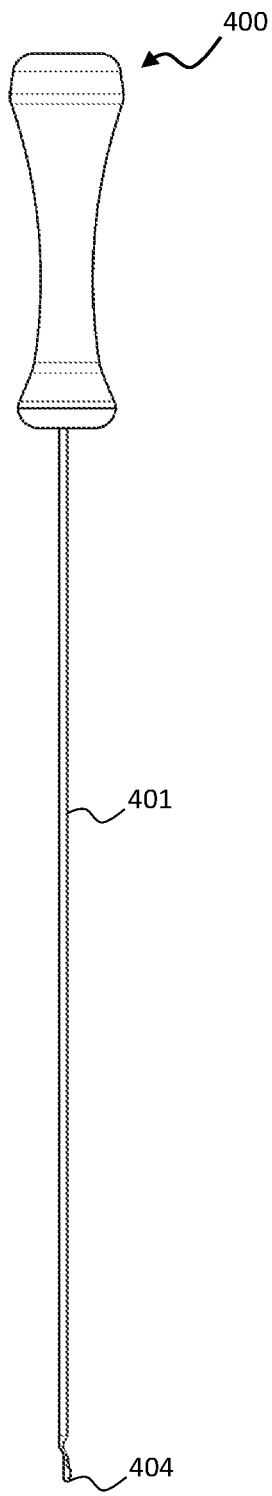
FIG. 17 is a side view of a nerve stimulating trocar.
Figure 18A:
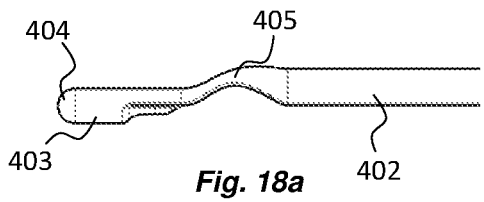
FIG. 18a is a partial side view of part of the nerve stimulating trocar of FIG. 17.
Figure 18B:
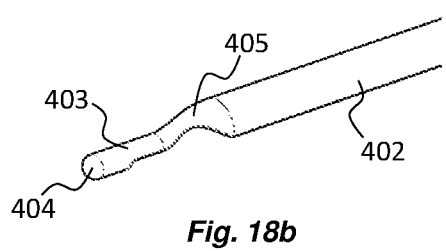
FIG. 18c is a perspective view of part of the nerve stimulating electrode of FIG. 17.

Turning to the method step depicted in FIG. 9g, once catheters 100 and 200 are implanted adjacent to respective pudendal nerve branches, the surgeon can then remove the part of the mat 500 which seals the anus by tearing frangible line 504.

The haemorrhoids may then be surgically removed. Once surgery has been completed, pump 750 is actuated and the medicament is drawn from the medicament reservoir 700 through the catheters 100 and 200 to the branches of the pudendal nerves on either side of the anus.

Figure 25:
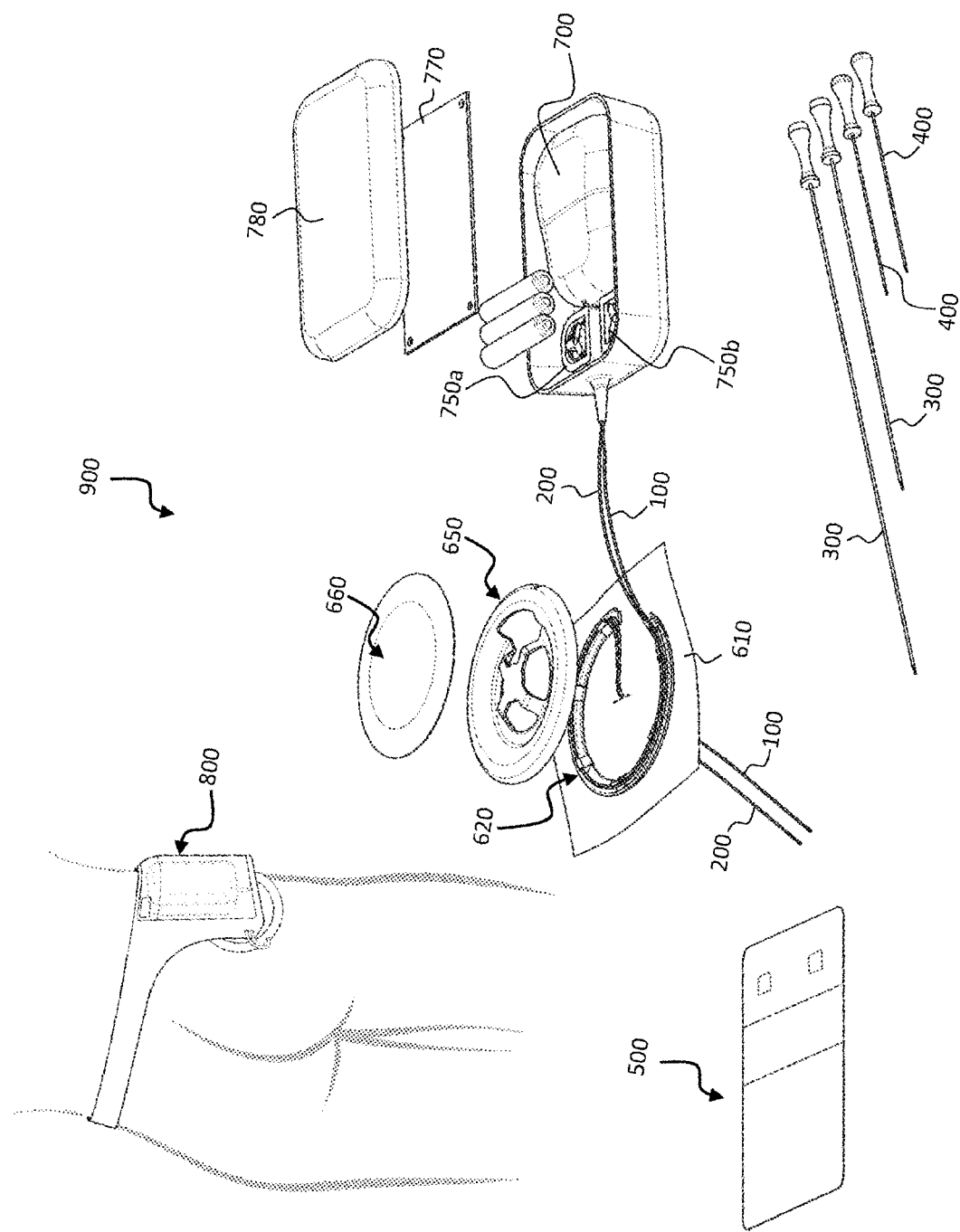
FIG. 25 illustrates the various part of a kit according to the present disclosure.

FIG. 25 shows the parts of the system in a kit 900 which includes the various parts of the system disclosed herein to allow the placement of catheters 100 and 200 adjacent to respective pudendal nerve branches to deliver medicament to a patient and alleviate pain after the surgical removal of haemorrhoids. Kit 900 comprises two catheters 100 and 200, retainer 600, two trocars 300 and two trocars 400, mat 500 and casing 710 housing medicament reservoir 700 and pump 750.

The invention claimed is:

1. A method for implanting a catheter to deliver medicament to a patient after haemorrhoid surgery, the method including:
   providing a catheter which extends from a proximal end to a distal end and has a sidewall which defines an internal lumen, said distal end having one or more apertures either in the sidewall or at the distal end for a release of the medicament into a target tissue site;
   connecting the distal end of the catheter to a stimulator trocar, the stimulator trocar comprising an elongate body which is made from a material having a greater rigidity than the catheter, the stimulator trocar comprising a nerve stimulator configured to stimulate nerves in the target tissue site;
   advancing the stimulator trocar and the catheter through a tissue of the patient;
   actuating the nerve stimulator at a determined frequency and adjusting a positioning of the stimulator trocar and the distal end of the catheter until a physical contraction of the external anal sphincter is observed at a frequency that correlates with the determined frequency of the nerve stimulator;
   identifying a location of the nerve stimulator and the distal end of the catheter where physical contraction of the external anal sphincter is achieved;

disconnecting the nerve stimulator from the catheter and withdrawing the nerve stimulator through a first incision leaving the distal end of the catheter implanted in the target tissue site.

2. The method of claim 1, wherein the target tissue site comprises tissue adjacent to the anal and/or rectal branches of the pudendal nerves.

3. The method of claim 1, wherein the medicament is selected from any one of bupivacaine, lidocaine, ropivacaine, buprenorphine, hydromorphone, ketobemidone, levomethadyl, levorphanol, mepiridine, methadone, morphine, nalbuphine, opium, oxycodone, pentazocine, phenoperidine, butorphanol, dextromoramide, dezocine, dextropropoxyphene, diamorphine, fentanyl, alfentanil, sufentanil, hydrocodone, piritramide, dextropropoxyphene, remifentanil, sufentanil, tilidine, tramadol, codeine, dihydrocodeine, meptazinol, dezocine, eptazocine, flupirtine, or a combination thereof.

4. The method of claim 1, wherein a second catheter is inserted into a different target tissue site, the second catheter extending from a proximal end to a distal end and having a sidewall which defines an internal lumen, the distal end of the second catheter having one or more apertures in the sidewall for the release of the medicament to the different target tissue site.

5. The method of claim 4, further comprising:
making a second incision on an opposite side of the anus to the first incision and tunnelling a trocar through the tissue from a lateral incision and across the midline of the patient towards the second incision, or from the second incision across the midline of the patient towards the lateral incision;
connecting a tip of the trocar to the proximal end of the second catheter and withdrawing the trocar through the tissue until a desired length of the second catheter is pulled through, and extends from, the lateral incision and the distal end of the second catheter extends from the second incision;
connecting the distal end of the second catheter to a second stimulator trocar, said second stimulator trocar being either the stimulator trocar or a different stimulator trocar;
advancing the second stimulator trocar and the second catheter through the tissue of the patient;
actuating a second nerve stimulator at a second determined frequency, said second determined frequency being either the determined frequency or a different determined frequency, wherein if the second stimulator trocar is the stimulator trocar then the second nerve stimulator is the nerve stimulator, and if the second stimulator trocar is the different stimulator trocar then said second nerve stimulator is a different nerve stimulator, wherein the different stimulator trocar comprises the different nerve stimulator and the different nerve stimulator is configured to stimulate nerves in the different target tissue site, and adjusting a positioning of the second stimulator trocar and the distal end of the second catheter until a physical contraction of the external anal sphincter is observed at a frequency that correlates with the second determined frequency of the second nerve stimulator;
identifying the location of the second nerve stimulator and the distal end of the second catheter where physical contraction of the external anal sphincter is achieved;
disconnecting the second nerve stimulator from the second catheter and withdrawing the second nerve stimulator through the first incision leaving the distal end of the second catheter implanted in the different target tissue site;
connecting the proximal end of the second catheter to a reservoir of the medicament and infusing the medicament through the internal lumen of the second catheter to deliver the medicament to the different target tissue site.

6. The method of claim 1 wherein the medicament is delivered in solution with a concentration between 0.25% and 0.75%.

7. The method of claim 1, wherein the medicament is delivered at a dose of between 1 ml and 40 ml per day.

8. The method of claim 7, wherein the medicament is delivered at a dose of 20 ml per day.

9. A method for positioning a catheter in a target tissue site to deliver a medicament to a patient after haemorrhoid surgery, the method including:
providing a catheter which extends from a proximal end to a distal end and has a sidewall which defines an internal lumen, the distal end of the catheter having one or more apertures either in the sidewall or at the distal end for a release of the medicament to the target tissue site;
making a lateral incision in the skin of a thigh of the patient and a first incision on one side of the anus;
tunnelling a trocar from the lateral incision through a tissue and towards the first incision, or from the first incision through the tissue and towards the lateral incision;
connecting a tip of the trocar to the proximal end of the catheter and withdrawing the trocar through the tissue until a desired length of the catheter is pulled through, and extends from, the lateral incision and the distal end of the catheter extends from the first incision;
connecting the distal end of the catheter to a stimulator trocar, the stimulator trocar comprising an elongate body which is made from a material having a greater rigidity than the catheter, the stimulator trocar comprising a nerve stimulator configured to stimulate nerves in the target tissue site;
advancing the stimulator trocar and the catheter through the tissue of the patient;
actuating the nerve stimulator at a determined frequency and adjusting the positioning of the stimulator trocar and the distal end of the catheter until a physical contraction of the external anal sphincter is observed at a frequency that correlates with the determined frequency of the nerve stimulator;
identifying a location of the nerve stimulator and the distal end of the catheter where physical contraction of the external anal sphincter is achieved;
disconnecting the nerve stimulator from the catheter and withdrawing the nerve stimulator through the first incision leaving the distal end of the catheter implanted in the target tissue site;
connecting the proximal end of the catheter to a reservoir of the medicament and infusing the medicament through the internal lumen of the catheter to deliver the medicament to the target tissue site.

10. The method of claim 9, wherein a second catheter is inserted into a different target tissue site, the second catheter extending from a proximal end to a distal end and having a sidewall which defines an internal lumen, the distal end of the second catheter having one or more apertures in the sidewall for a release of the medicament to the different target tissue site.

11. The method of claim 10, further comprising:

making a second incision on an opposite side of the anus to the first incision and tunnelling a trocar through the tissue from the lateral incision and across the midline of the patient towards the second incision, or from the second incision across the midline of the patient towards the lateral incision;

connecting a tip of the trocar to the proximal end of the second catheter and withdrawing the trocar through the tissue until a desired length of the second catheter is pulled through, and extends from, the lateral incision and the distal end of the second catheter extends from the second incision;

connecting the distal end of the second catheter to a second stimulator trocar, said second stimulator being either the stimulator trocar or a different stimulator trocar;

advancing the second stimulator trocar and the second catheter through the tissue of the patient;

actuating a second nerve stimulator at a second determined frequency, said second determined frequency being either the determined frequency or a different determined frequency, wherein if the second stimulator trocar is the stimulator trocar then the second nerve stimulator is the nerve stimulator, and if the second stimulator trocar is the different stimulator trocar then said second nerve stimulator is a different nerve stimulator, wherein the different stimulator trocar comprises the different nerve stimulator and the different nerve stimulator is configured to stimulate nerves in the different target tissue site, and adjusting the positioning of the second stimulator trocar and the distal end of the second catheter until a physical contraction of the external anal sphincter is observed at a frequency that correlates with the second determined frequency of the second nerve stimulator;

identifying the location of the nerve stimulator and the distal end of the second catheter where physical contraction of the external anal sphincter is achieved;

disconnecting the second nerve stimulator from the second catheter and withdrawing the second nerve stimulator through the first incision leaving the distal end of the second catheter implanted in the different target tissue site;

connecting the proximal end of the second catheter to a reservoir of the medicament and infusing the medicament through the internal lumen of the second catheter to deliver the medicament to the different target tissue site.

12. The method of claim 9, wherein the target tissue site comprises tissue adjacent to the anal and/or rectal branches of the pudendal nerves.

13. The method of claim 9, wherein the medicament is selected from any one of bupivacaine, lidocaine, ropivacaine, buprenorphine, hydromorphone, ketobemidone, levomethadyl, levorphanol, mepiridine, methadone, morphine, nalbuphine, opium, oxycodone, pentazocine, phenoperidine, butorphanol, dextromoramide, dezocine, dextropropoxyphene, diamorphine, fentanyl, alfentanil, sufentanil, hydrocodone, piritramide, dextropropoxyphene, remifentanil, sufentanil, tilidine, tramadol, codeine, dihydrocodeine, meptazinol, dezocine, eptazocine, flupirtine, or a combination thereof.

14. The method of claim 9, wherein the medicament is delivered in solution with a concentration between 0.25% and 0.75%.

15. The method of claim 9, wherein the medicament is delivered at a dose of between 1 ml and 40 ml per day.

16. The method of claim 15, wherein the medicament is delivered at a dose of 20 ml per day.

* * * * *

UNITED STATES PATENT AND TRADEMARK OFFICE
CERTIFICATE OF CORRECTION

| | |
|---|---|
| PATENT NO. | : 11,524,140 B2 |
| APPLICATION NO. | : 16/971115 |
| DATED | : December 13, 2022 |
| INVENTOR(S) | : David Zachary Lubowski et al. |

It is certified that error appears in the above-identified patent and that said Letters Patent is hereby corrected as shown below:

In the Claims

Claim 3, Column 19, Line 11, delete "mepiridine" and insert --meperidine--.

Claim 11, Column 22, Line 1, delete "nerve" and insert --second nerve--.

Claim 13, Column 22, Line 20, delete "mepiridine" and insert --meperidine--.

Signed and Sealed this
Twenty-eighth Day of March, 2023

Katherine Kelly Vidal
*Director of the United States Patent and Trademark Office*